United States Patent
Varum et al.

(10) Patent No.: US 12,419,843 B2
(45) Date of Patent: Sep. 23, 2025

(54) METHOD FOR PREPARING A SOLID DOSAGE FORM COMPRISING ANTIBODIES BY WET GRANULATION, EXTRUSION AND SPHERONIZATION

(71) Applicant: Tillotts Pharma AG, Rheinfelden (CH)

(72) Inventors: Felipe Varum, Rheinfelden (CH); Sophie Decollogny, Basel (CH); Roberto Bravo, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 954 days.

(21) Appl. No.: 16/646,336

(22) PCT Filed: Sep. 11, 2018

(86) PCT No.: PCT/EP2018/074521
§ 371 (c)(1),
(2) Date: Mar. 11, 2020

(87) PCT Pub. No.: WO2019/057563
PCT Pub. Date: Mar. 28, 2019

(65) Prior Publication Data
US 2020/0268675 A1    Aug. 27, 2020

(30) Foreign Application Priority Data
Sep. 20, 2017   (EP) .................................... 17192259

(51) Int. Cl.
| | |
|---|---|
| *A61K 9/50* | (2006.01) |
| *A61K 9/00* | (2006.01) |
| *A61K 9/14* | (2006.01) |
| *A61K 9/48* | (2006.01) |
| *C07K 16/24* | (2006.01) |

(52) U.S. Cl.
CPC .......... *A61K 9/5073* (2013.01); *A61K 9/0004* (2013.01); *A61K 9/14* (2013.01); *A61K 9/4858* (2013.01); *A61K 9/4866* (2013.01); *A61K 9/5015* (2013.01); *A61K 9/5026* (2013.01); *A61K 9/5089* (2013.01); *C07K 16/241* (2013.01)

(58) Field of Classification Search
None
See application file for complete search history.

(56) References Cited

U.S. PATENT DOCUMENTS

| | | | | |
|---|---|---|---|---|
| 5,286,493 | A  * | 2/1994 | Oshlack | A61K 9/5026 |
| | | | | 424/483 |
| 2005/0053598 | A1* | 3/2005 | Burke | A61P 1/14 |
| | | | | 424/130.1 |
| 2006/0246192 | A1 | 11/2006 | Dukic et al. | |
| 2010/0047340 | A1* | 2/2010 | McGinity | A61K 9/2081 |
| | | | | 702/155 |
| 2012/0282249 | A1* | 11/2012 | Fox | A61P 29/00 |
| | | | | 424/133.1 |
| 2017/0189527 | A1* | 7/2017 | Rinaldi | A61P 1/00 |

FOREIGN PATENT DOCUMENTS

| | | |
|---|---|---|
| JP | 2006-312630 | 11/2006 |
| WO | WO 1999/45903 A1 | 9/1999 |
| WO | WO 2002/35991 A2 | 5/2002 |
| WO | WO 2007/112579  * | 10/2007 |
| WO | WO 2012/130872 A1 | 10/2012 |

OTHER PUBLICATIONS

Strickley, Robert G. et al., "A Review of Formulations of Commercially Available Antibodies", Journal of Pharmaceutical Sciences, 110 (2021) 2590-2608.
Auffray, Julie et al., "Development of Monoclonal Antibodies in Tablet Form: A New Approach for Local Delivery", International Journal of Pharmaceutics, 661 (2024): 124423.
Muley, Sagar et al., "Extrusion-Spheronization a Promising Pelletization Technique: In-Depth Review", Asian Journal of Pharmaceutical Sciences II (2016) 684-699.

* cited by examiner

*Primary Examiner* — Tigabu Kassa
(74) *Attorney, Agent, or Firm* — Smith Patent, LLC; Chalin A. Smith

(57) ABSTRACT

The present invention relates to a method for preparing immediate and sustained release solid dosage forms, comprising antibodies and functional fragments thereof, by wet granulation, extrusion and spheronization, optionally coated with a delayed release coating the solid dosage forms prepared by the method and the use of the solid dosage forms in the topical treatment in the gastrointestinal tract of a patient.

16 Claims, 8 Drawing Sheets

(A)

(B)

(C)

(A)

(B)

(A)

(B)

METHOD FOR PREPARING A SOLID DOSAGE FORM COMPRISING ANTIBODIES BY WET GRANULATION, EXTRUSION AND SPHERONIZATION

PRIORITY

This application corresponds to the U.S. National phase of International Application No. PCT/EP2018/074521, filed Sep. 11, 2018, which, in turn, claims priority to European Patent Application No. 17.192259.4 filed Sep. 20, 2017, the contents of which are incorporated by reference herein in their entirety.

FIELD OF THE INVENTION

The present invention relates to a method for preparing immediate and sustained release solid dosage forms, comprising antibodies and functional fragments thereof, by wet granulation, extrusion and spheronization, optionally coated with a delayed release coating, the solid dosage forms prepared by the method and the use of the solid dosage forms in the topical treatment in the gastrointestinal tract of a patient.

BACKGROUND

Numerous pharmaceutical compositions prepared by various methods have been proposed and in some cases implemented comprising biologically active polypeptides like enzymes or hormones. Such biologically active polypeptides, in particular large polypeptides with antigen binding activity such as antibodies and functional fragments thereof, due to their intrinsic nature, are sensitive to any change in their environment, giving rise to inherent instability. Therefore, ensuring their stability and activity as well as the therapeutically efficacious release upon incorporation into a pharmaceutical compositions is very challenging and yet paramount due to the prohibitive costs of such antibodies in quantities that allow their therapeutic application in a patient. Generally, this inherent instability of antibodies is independent of whether they are used to prepare a pharmaceutical composition in a liquid, gelatinous, semi-solid, solid or any other form. However, in particular for solid dosage forms, many processing steps in the manufacture can be detrimental for stability and activity of an antibody or functional fragment thereof.

The use of solid dosage forms is very common for pharmaceutical compositions intended for enteral administration. Enteral administration, and especially oral administration, of solid dosage forms comprising biologically active polypeptides has become increasingly important in recent years, particularly with regards to convenience and safety, as it further allows for the topical treatment of symptoms of diseases of the gastrointestinal tract, as for example inflammatory bowel disease (IBD), colorectal cancer, diarrhea or microbial infections.

Many factors may affect the chemical and physical stability and thereby the activity of large biologically active polypeptides like antibodies and functional fragments thereof during the incorporation into a solid dosage form. Chemical instability of large polypeptides, e.g. in the form of fragmentation, oxidation, deamination, isomerization, disulfide bond formation or formation of acidic/basic species, is directly affected by ingredients used in the solid dosage form, as well as by pH and temperature during the preparation and later storage of the solid dosage form. Physical instability, e.g. in the form of denaturation, aggregation or adsorption, can result from shear stress, changes in temperature, or high shear forces during preparation and later storage. For example already a moderately elevated temperature of greater than 55° C. has been shown to cause denaturation of immunoglobulin G (IgG) thereby affecting the integrity of the polypeptide, with the antigen binding fragment (Fab) being part of the polypeptide most sensitive to the elevated temperature (Vermeer et al., Biophys J., 2000 Jan., 78(1): 394-404). Biological instability, e.g. in the form of proteolytic digestion or post-translational modification, can result from the exposure to proteases and other enzymes, as well as other biological factors able to affect the integrity of large polypeptides. The processing of large biologically active polypeptides, such as antibodies and functional fragments thereof, in order to incorporate them into solid dosage forms, therefore poses major challenges, in particular with regard to the choice of individual excipients as well as with regard to the processing parameters.

In addition to directly affecting stability and activity of the large biologically active polypeptide, the choice of the method for preparing the solid dosage form will also affect the properties of the resulting solid dosage form, i.e. its stability, integrity, quality and dissolution behavior. Compared to other methods for preparing solid dosage forms, extrusion-spheronization allows for high levels of active components without producing excessively larger particles (in contrast for example to solid dosage forms prepared by direct compression), easy combination of two or more active agents, easy modification of the physical characteristics of the active ingredients and excipients, and particles having high bulk density, low hygroscopicity, high sphericity, narrow particle size distribution and smoother surface (Sahoo et al., J. Pharm. Res. Opin., 9 (2013), pp. 65-68).

Methods for preparing solid dosage forms by extrusion-spheronization are known in the art. Melt extrusion-spheronization methods as disclosed in EP 1 064 935, WO00/24382, EP 1 996 163, EP 1 083 196, EP 2 066 309, EP 1 171 101, EP 1 166 776 or EP 1 978 940 are unsuitable for use with antibodies and functional fragments thereof. During melt-extrusion a melt is formed of the mixture of all ingredients, which would include the antibodies and functional fragments, at an elevated temperature. This melt is then extruded at a similarly elevated temperature. These elevated temperatures tend to be well above 55° C. Other extrusion spheronization methods described in the prior art use combinations of excipients, specific parameters for some of the processing steps as well as additional processing steps that can negatively affect activity and recovery of antibodies and functional fragments thereof. EP 2 144 599 discloses a composition, comprising a wax-like agent with a melting point between 40° C. and 120° C., prepared by a an extrusion-spheronization method, where the composition in a last step is heated 15-20° C. above the melting point of the wax-like agent to melt it. EP 0 935 523 discloses a method for embedding and encapsulating an active component in a matrix, comprising plasticizing a matrix material upon heating to form a melt, which needs to be cooled down before an active component can be admixed. The mixture of matrix melt and active component is then extruded and cut or molded into pieces.

These methods for preparing solid dosage forms by extrusion-spheronization known in the art tend to be unsuitable for the use with large bioactive polypeptides like antibodies and functional fragments thereof. The high temperatures, temperature changes, shear forces and/or pressure during the individual steps of melting/granulation, extrusion, spheronization and drying of the solid dosage form render these methods unsuitable for antibodies and functional fragments thereof, due to the detrimental effect on stability and activity of the antibodies and functional fragments thereof. Moreover, the inherent binding capacity of antibodies and functional fragments thereof, tends to give rise to strong physical/chemical interactions with many excipients used for the preparation of such solid dosage forms, resulting in release of only a fraction of the dose of antibody or functional fragment thereof from the dissolving solid dosage form upon administration.

The recovery of antibodies or functional fragments from solid dosage forms may be further diminished by the use of polymers for a prolonged release of the antibody or functional fragment thereof (i.e. sustained release polymers). In IBD, like ulcerative colitis or Crohn's disease, for inflamed colonic mucosa to be exposed to an antibody concentration effective for topical treatment, the antibody must retain sufficient stability and activity until it is taken up by the target mucosa. In order to minimize antibody degradation in the colonic luminal fluids (Yadav et al., International Journal of Pharmaceutics, 2016. 502(12): p. 181-187), a slow release of antibodies or functional fragments thereof from a solid dosage form is desirable. This would ensure the release of the antibody or functional fragment thereof from the solid dosage form at a rate that allows the effective uptake into mucosa and a continuous provision of antibody or functional fragment thereof over several hours or days. Moreover, it would allow the treatment of a greater target area of inflamed mucosa, as it would allow the solid dosage form to release antibodies or functional fragments thereof while moving along the inside of the gastrointestinal tract.

Gastrointestinal transit, in particular, colonic transit of solid dosage forms shows a wide inter- and intra-individual variability (Varum et al., Int. J. Pharm., 2010. 395(1-2): p. 26-36). Furthermore, IBD conditions such as ulcerative colitis or Crohn's disease can also influence transit time. It has been shown that in some cases colonic transit is prolonged in ulcerative colitis, in the areas proximal to the inflamed mucosa. Thus a dosage form will stay in those areas longer, before reaching the inflamed mucosa. If the antibody is not provided in a stable enough form this could mean premature antibody degradation leading to reduced levels of antibody reaching the distal colonic mucosa. On the other hand, transit through the inflamed area can be accelerated in some cases, which further complicates the design of a dosage form for an efficient antibody delivery to the ileum and the large intestine.

Due to the biopharmaceutical advantages of multiparticulates over single units, such as longer colonic transit than single units and wider spread of dose in multiple small units (Varum et al., Int. J. Pharm., 2010. 395(1-2): p. 26-36), a multiparticulate drug delivery system would be a preferred choice. Single units of such a multiparticulate drug delivery system could be designed to achieve sustained antibody release.

Thus, there is a need for a method for preparing a solid dosage form, which can be used for the preparation of a multiparticulate solid dosage, by extrusion-spheronization comprising antibodies or functional fragments thereof that minimizes loss of biological activity of the antibody or functional fragment thereof used for the preparation of the solid dosage form. In particular, the method should preserve stability and activity of the antibody or functional fragment thereof during individual steps of the preparation, allow release over a short or a prolonged period of time, and reduce interactions of the antibody or functional fragment thereof with other ingredients of the solid dosage form that limits antibody recovery.

SUMMARY OF THE INVENTION

After testing various processing conditions and excipients the present inventors found an advantageous method for preparing a solid dosage form comprising at least one antibody or functional fragment thereof by wet granulation, extrusion and spheronization. This method preserves stability and activity of the antibodies or functional fragments thereof used for the preparation and ensures that an optimal amount of the antibody or functional fragment thereof can be recovered from the solid dosage form upon dissolution.

Thus, the present invention provides a novel method for preparing a solid dosage form, comprising at least one antibody or functional fragment thereof, prepared by wet granulation, extrusion and spheronization. The present invention relates to the subject matter defined in the following items 1 to 77:

[1] A method for preparing a solid dosage form comprising at least one antibody or functional fragment thereof, a surfactant, an extrusion-spheronization aid, a buffer, a disintegrant and at least one further excipient selected from the group consisting of fillers, sustained release agents and combinations thereof, comprising the steps of
  a) providing a powder blend comprising the extrusion-spheronization aid, the disintegrant, and the at least one further excipient;
  b) wet granulating by adding a binding liquid to the powder blend of step a) to obtain a wet mass;
  c) extruding the wet mass of step b) and collecting an extrudate;
  d) spheronizing the extrudate of step c) to obtain wet spheroids;
  e) drying the wet spheroids to obtain the solid dosage form;
  wherein the powder blend and/or the binding liquid comprises the at least one antibody or functional fragment thereof, the buffer and the surfactant.

[2] Method according to item 1, wherein the solid dosage form is a pellet, bead, mini sphere, granule or mini tablet, preferably a pellet.

[3] Method according to item 1 or 2, wherein the extrusion-spheronization aid is microcrystalline cellulose, hydroxypropylmethylcellulose (HPMC), hydroxyethylcellulose, cyclodextrin, pectin, pectinic acid, starch, dextrins, carrageenan, glycerol monostearate or colloidal silica dioxide, preferably microcrystalline cellulose (e.g., Avicel® PH-101).

[4] Method according to any of the preceding items, wherein the disintegrant is selected from sodium starch glycolate, croscarmellose sodium, cross-linked polyvinylpyrrolidone, soy polysaccharide and cross-linked alginic acid, preferably sodium starch glycolate.

[5] Method according to any of the preceding items, wherein the at least one further excipient is selected from the group consisting of fillers selected from dextrose, lactose, lactose monohydrate, lactose anhydrous, xylitol, mannitol, sucrose, glucose, raffinose, sorbitol, trehalose, dicalcium phosphate, oxides of magnesium or silicon, titanium carbonate, calcium carbonate, magnesium phosphate, porous calcium phosphate or porous magnesium phosphate, amino acids such as arginine, histidine, glycine, alanine, lysine, proline, leucine, glutamic acid, serine, aspartic acid and asparagine and respective salts thereof, propyleneglycol, and polyethylene glycol; and of sustained release agents in the form of sustained release polymers selected from nonionic poly(ethylene oxide) polymers with a molecular weight between 100,000 and 7,000,000, preferably a molecular weight of about 100,000 (e.g. Polyox® N-10NF), HPMC 2208 type with a viscosity at 2 wt.-% in water at 20° C. between 3 and 100,000 mPa·s (such as Methocel K3 Premium LV, Methocel K100 Premium LV, Methocel K4M Premium, Methocel K15 Premium, Methocel K100M Premium), preferably between about 2,308 and 9,030 mPa·s (e.g. Methocel K4M Premium and Methocel K15M Premium), more preferably between about 2,663 and 4,970 mPa·s (e.g. Methocel K4M Premium), chitosan, xanthan gum, guar gum, tragacanth, locust been gum, acacia gum, carbomers glyceryl (di)behenate (e.g. Compritol® 888 ATO), glyceryl palmitostearate (e.g. Precirol®), and polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D, Eudragit® NM 30D); polyvinyl acetate (Kollicoat® SR 30D); ethylcellulose; and combinations thereof.

[6] Method according to item 5, wherein the solid dosage form is an immediate release solid dosage form, and the at least one further excipient is a filler selected from the group consisting of dextrose, lactose, lactose monohydrate, lactose anhydrous, mannitol, sorbitol, xylitol, sucrose, glucose, raffinose, trehalose, dicalcium phosphate, oxides of magnesium or silicon, titanium carbonate, calcium carbonate, magnesium phosphate, porous calcium phosphate or porous magnesium phosphate, amino acids such as arginine, histidine, glycine, alanine, lysine, proline, leucine, glutamic acid, serine, aspartic acid and asparagine, and respective salts thereof, propylene glycol, polyethylene glycol, and combinations thereof; preferably dextrose, sucrose, mannitol, sorbitol, xylitol, trehalose, amino acids such as arginine, histidine, glycine, alanine, lysine, proline, leucine, glutamic acid, serine, aspartic acid and asparagine, and respective salts thereof, dicalcium phosphate, and combinations thereof; more preferably sorbitol, trehalose, sucrose, mannitol, or amino acids such as arginine, histidine, glycine, alanine, lysine, proline, leucine, glutamic acid, serine, aspartic acid and asparagine, and respective salts thereof, and combinations thereof; even more preferably sorbitol.

[7] Method according to item 6, the powder blend in step a) comprising
  i) microcrystalline cellulose as extrusion-spheronization aid;
  ii) sodium starch glycolate, as disintegrant; and
  iii) sorbitol, sucrose, trehalose or mannitol, preferably sorbitol, as filler.

[8] Method according to any one of items 1 to 7, the powder blend in step a) comprising
  i) 20 to 90%, preferably 30 to 80%, more preferably 40 to 75%, even more preferably 45 to 70%, most preferably 45 to 50% extrusion-spheronization aid;
  ii) 0.5 to 50%, preferably 0.5 to 40%, more preferably 1 to 35%, even more preferably 1 to 30%, even more preferably 1 to 15%, most preferably about 1 to 10%, alternatively most preferably 10 to 30%, of the disintegrant;
  iii) 2.5 to 50%, preferably 5 to 50%, more preferably 10 to 40%, even more preferably 20 to 40%, most preferably 30 to 40%, alternatively most preferably 20 to 30%, of a filler (preferably sucrose, trehalose, sorbitol, mannitol, or amino acids such as arginine, histidine, glycine, alanine, lysine, proline, leucine, glutamic acid, serine, aspartic acid and asparagine and respective salts thereof, and combinations thereof) as the at least one further excipient; and wherein the solid dosage form is an immediate release solid dosage form.

[9] Method according to any one of items 1 to 7, the powder blend in step a) comprising
  i) 20 to 70%, preferably 30 to 60%, more preferably 40 to 50%, even more preferably about 45%, extrusion-spheronization aid;
  ii) 0.5 to 30%, preferably 0.5 to 20%, more preferably 1 to 15%, even more preferably 1 to 10%, of the disintegrant;
  iii) 5 to 50%, preferably 10 to 45%, more preferably 20 to 40%, even more preferably 30 to 40%, of a filler (preferably sucrose, trehalose, sorbitol, mannitol, or amino acids such as arginine, histidine, glycine, alanine, lysine, proline, leucine, glutamic acid, serine, aspartic acid and asparagine, and respective salts thereof, and combinations thereof) as the at least one further excipient;
  iv) 0.1 to 30%, preferably 1 to 20%, more preferably 2 to 15% even more preferably 5 to 15% of the at least one antibody or functional fragment thereof; and wherein the solid dosage form is an immediate release solid dosage form.

[10] Method according to items 1 to 9, further comprising, after step e), the step of
  f) applying at least one additional coating in the form of a sustained release coating.

[11] Method according to item 10, wherein the sustained release coating comprises at least one sustained release polymer selected from the group consisting of polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D and Eudragit® NM 30D), ethylcellulose, polyvinyl acetate (e.g. Kollicoat® SR 30D), and combinations thereof.

[12] Method according to any one of items 1 to 5, wherein the solid dosage form is a sustained release dosage form, and wherein the at least one further excipient comprises at least one sustained release agent.

[13] Method according to item 12, wherein the at least one sustained release agent is a sustained release polymer selected from the group consisting of nonionic poly(ethylene oxide) polymers with a molecular weight between 100,000 and 7,000,000, preferably a molecular weight of about 100,000 (e.g. Polyox® N-10NF); HPMC 2208 type with a viscosity at 2 wt.-% in water at 20° C. between 3 and 100,000 mPa·s (such as Methocel K3 Premium LV, Methocel K100 Premium LV, Methocel K4M Premium, Methocel K15 Premium, Methocel K100M Premium), preferably between about 2,308 and 9,030 mPa·s (e.g. Methocel K4M Premium and Methocel K15M Premium), more preferably between about 2,663 and 4,970 mPa·s (e.g. Methocel K4M Premium); chitosan; xanthan gum; guar gum; tragacanth; locust been gum; acacia gum; carbomers; glyceryl (di)behenate (e.g. Compritol® 888 ATO); glyceryl palmitostearate (e.g. Precirol®); polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D, Eudragit® NM 30D); polyvinyl acetate (Kollicoat® SR 30D), ethylcellulose; and combinations thereof; preferably, Polyox® N-10NF, Methocel K4M and Compritol® 888 ATO and the like.

[14] Method according to item 13, the powder blend in step a) comprising
i) microcrystalline cellulose as extrusion-spheronization aid;
ii) sodium starch glycolate, as disintegrant; and
iii) Polyox N-10NF or Methocel K4M as the at least one further excipient.

[15] Method according to any one of items 1 to 5 and 9 to 14, the powder blend in step a) comprising
i) 20 to 90%, preferably 45 to 80%, more preferably 50 to 80%, even more preferably 60 to 75%, most preferably about 70 to 75% extrusion-spheronization aid
ii) 0.1 to 45%, preferably 0.5 to 35%, more preferably 1 to 30%, even more preferably 1 to 25%, even more preferably 1 or 15%, most preferably about 5 to 15% of the disintegrant;
iii) 0.5 to 30%, preferably 1 to 20%, more preferably 2.5 to 12.5%, even more preferably 2.5 to 10%, most preferably about 2.5 to 7.5%, of the at least one further excipient comprising at least one sustained release agent; and
wherein the solid dosage form is a sustained release solid dosage form.

[16] Method according to any of the preceding items, comprising at least two further excipients, wherein the first further excipient is a sustained release polymer and the second further excipient is a filler, preferably selected from sorbitol or mannitol, more preferably sorbitol.

[17] Method according to item 16, the powder blend in step a) comprising
i) 20 to 90%, preferably 45 to 85%, more preferably 50 to 80%, even more preferably 60 to 80%, most preferably about 75% extrusion-spheronization aid;
ii) 0.1 to 40%, preferably 0.5 to 30%, more preferably 1 to 20%, even more preferably 1 to 15%, most preferably about 1 to 10% of the disintegrant;
iii) 1 to 30%, preferably 1 to 20%, more preferably 2.5 to 12.5%, even more preferably 2.5 to 10%, most preferably about 2.5 to 7.5%, of the first further excipient comprising at least one sustained release agent;
iv) 0.5 to 50%, preferably 1 to 20%, more preferably 1 to 15%, even more preferably 5 to 15%, most preferably about 10%, of the filler; and
wherein the solid dosage form is a sustained release solid dosage form.

[18] Method according to item 17, the powder blend in step a) comprising
i) microcrystalline cellulose as extrusion-spheronization aid;
ii) glyceryl (di)behenate as first further excipient; and
iii) sorbitol, sucrose, trehalose, mannitol, or amino acids such as arginine, histidine, glycine, alanine, lysine, proline, leucine, glutamic acid, serine, aspartic acid and asparagine, and respective salts thereof, and combinations thereof, preferably sorbitol, as filler.

[19] Method according to item 16, 17 or 18, the powder blend in step a) comprising
i) 30 to 85%, preferably 45 to 80%, more preferably 50 to 80%, even more preferably about 75% extrusion-spheronization aid;
ii) 0.1 to 40%, preferably 0.5 to 30%, more preferably 1 to 20%, even more preferably 1 to 15%, most preferably 1 to 10% of the disintegrant;
iii) 1 to 35%, preferably 1 to 25%, more preferably 2.5 to 15%, even more preferably about 2.5 to 10%, of glyceryl (di)behenate as the first further excipient;
iv) 2.5 to 50%, preferably 5 to 40%, more preferably 10 to 35%, even more preferably 10 to 25%, of the second further excipient in the form of a filler, preferably sucrose, trehalose, sorbitol or mannitol, more preferably sorbitol; and
wherein the solid dosage form is a sustained release solid dosage form.

[20] Method according to any of the preceding items, wherein the powder blend in step a) and/or the binding liquid in step b) comprise at least one further additive selected from glidants, plasticizers, antioxidants, stabilizers, humectants, protective colloids, dyes, permeation enhancers, protease inhibitors, and combinations thereof.

[21] Method according to any of the preceding items, wherein the solid dosage form comprises an amount of the at least one antibody or functional fragment thereof that allows the administration of a therapeutically effective dose of the at least one antibody or functional fragment thereof as a single unit dose.

[22] Method according to any of the preceding items, wherein the solid dosage form comprises from 0.01 to 60%, preferably from 0.05 to 45%, more preferably from 0.1 to 30%, even more preferably from 0.5 to 25%, even more preferably from 1 to 20%, even more preferably from 1 to 15%, most preferably 5 to 15%, of the at least one antibody or functional fragment thereof, relative to the total weight of the solid dosage form.

[23] Method according to any of the preceding items, wherein the functional antibody fragment is a Fab fragment, a F(ab')$_2$ fragment, a Fab' fragment, an scFv, a dsFv, a VHH, a diabody, a triabody, a tetrabody, an Fc fusion protein or a minibody.

[24] Method according to any of the preceding items, wherein the at least one antibody or functional fragment thereof is selected from antibodies specific to tumor necrosis factor alpha (TNFα) and functional fragments thereof, antibodies specific to α4β7 integrin and functional fragments thereof, antibodies specific to CD3, CD4 or CD20 and functional fragments thereof, antibodies specific to interleukin 6 (IL-6), interleukin 12 (IL-12), interleukin 13 (IL-13), interleukin 23 (IL-23) or to their receptors and functional fragments thereof, antibodies specific to CXCL10/IP-10 and functional fragments thereof, and antibodies specific to p40 protein subunit and functional fragments thereof.

[25] Method according to any of the preceding items, wherein the antibody or functional fragment thereof is suitable for use in the treatment of a gastrointestinal disease, preferably an inflammatory bowel disease (IBD), celiac disease, a gastrointestinal infection, colorectal cancer or small intestine cancer, more preferably an IBD like Crohn's disease or ulcerative colitis.

[26] Method according to any of the preceding items, wherein the at least one antibody or functional fragment thereof is selected from infliximab, adalimumab, etanercept, certolizumab pegol, golimumab, visilizumab, eldelumab, abrilumab, canakinumab, tocilizumab, ustekinumab, natalizumab, etrolizumab, priliximab, vedolizumab and functional fragments thereof; from anti-TNFα antibodies or functional fragments thereof with light chain variable domains and/or heavy chain variable domains comprising complementarity-determining regions (CDRs) with amino acid sequences as disclosed in claim 2 of PCT/EP2017/056218, in claim 2 of PCT/EP2017/056246, in claim 2 of PCT/EP2017/056237 and/or in claim 2 of PCT/EP2017/056227, as originally filed; from anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, and claim 4 of PCT/EP2017/056227, as originally filed; and combinations thereof.

[27] Method according to any one of items 1 to 26, wherein the antibody or functional fragment thereof is selected from antibodies specific to TNFα and functional fragments thereof.

[28] Method according to item 27, wherein the antibody specific to TNFα or functional fragment thereof is selected from infliximab, adalimumab, etanercept, certolizumab pegol and golimumab and functional fragments thereof; from anti-TNFα antibodies or functional fragments thereof with light chain variable domains and/or heavy chain variable domains comprising complementarity-determining regions (CDRs) with amino acid sequences as disclosed in claim 2 of PCT/EP2017/056218, in claim 2 of PCT/EP2017/056246, in claim 2 of PCT/EP2017/056237 and/or in claim 2 of PCT/EP2017/056227, as originally filed; from anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, and claim 4 of PCT/EP2017/056227, as originally filed; and combinations thereof.

[29] Method according to any of the preceding items, wherein the at least one antibody or functional fragment thereof is comprised in the binding liquid in a concentration (w/v) of 0.01 to 1000 mg/ml, preferably 0.1 to 500 mg/ml, more preferably 0.1 to 200 mg/ml, even more preferably 0.1 to 100 mg/ml, even more preferably 1 to 100 mg/ml, even more preferably 5 to 100 mg/ml, even more preferably 10 to 50 mg/ml.

[30] Method according to any of the preceding items, wherein the binding liquid is an aqueous solution.

[31] Method according to any of the preceding items, wherein the amount of surfactant relative to the total volume of the binding liquid (w/v) is from 0.005 to 2.0%, preferably 0.01 to 1%, more preferably 0.05 to 0.8%, even more preferably 0.05 to 0.5%, even more preferably 0.1 to 0.5, most preferably about 0.1% based on the total volume of the binding liquid; or wherein the concentration (w/w) of the surfactant in the solid dosage form is from 0.001 to 1%, preferably from 0.005 to 0.5%, more preferably from 0.01 to 0.5%, even more preferably from 0.01% to 0.25%, based on the total weight of the solid dosage form after step e).

[32] Method according to any of the preceding items, wherein the surfactant is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 hydroxystearate, caprylocaproyl macrogol-8 glyceride, D-α-tocopherol polyethylene glycol 1000 succinate, glyceryl monostearate, lecithin, sorbitan monopalmitate, cetyl alcohol, ( )eyl alcohol, sodium glycolate, sodium de(s)oxycholate, polyethylene glycol, polypropylene glycol, alkyl poly(ethylene oxide), alkyl glycoside, alkyl polyglucoside, octyl glucoside, decyl maltoside, and combinations thereof, preferably polysorbate 20 or poloxamer 188, more preferably polysorbate 20.

[33] Method according to any of the preceding items, wherein binding liquid comprises the surfactant.

[34] Method according to any of the preceding items, wherein the buffer comprised in the powder blend and/or the binding liquid is selected from acetate, citrate, histidine, hydroxymethylaminomethane (TRIS), and phosphate buffers (buffer salts), and combinations thereof.

[35] Method according to any of the preceding items, wherein the powder blend of step a) or the binding liquid of step b) further comprises a binder, preferably selected from hydroxypropyl methylcellulose, hydroxypropyl cellulose, methyl cellulose, polyvinylpyrrolidone and combinations thereof.

[36] Method according to any of the preceding items, wherein the wet mass from step b) is extruded using a screw extruder.

[37] Method according to any of the preceding items, wherein the disintegrant increases the uptake capacity of the powder blend from step a) for the binding liquid comprising the antibody or functional fragment thereof.

[38] Method according to any of the preceding items, wherein at any time during steps a) to d) the temperature of the antibody or functional fragment thereof is lower than 55° C., preferably lower than 50° C., more preferably lower than 45° C., even more preferably lower than 40° C., even more preferably lower than 35° C., most preferably lower than 30° C.

[39] Method according to any of the preceding items, wherein during step e) the drying of the wet spheroids is carried out at a temperature lower than 55° C., preferably lower than 50° C., more preferably lower than 45° C., even more preferably at about 40° C.

[40] Method according to item 39, wherein during step e) the drying of the wet spheroids is carried out at a temperature lower than 45° C. using vacuum-assisted drying.
[41] Method according to any of the preceding items, wherein after drying in step e), the residual solvent content (i.e. residual moisture level) of the solid dosage form is less than 15 wt.-%, preferably less than 10 wt.-%, more preferably less than 8 wt.-%, even more preferably less than 5 wt.-%, even more preferably less than 3 wt.-%, even more preferably less than 2%, relative to the total weight of the solid dosage form.
[42] Method according to any of the above items, wherein the solid dosage form is intended for oral or rectal, preferably oral, administration.
[43] Method according to any of the above items, comprising a further step, after drying in step e), or after step f) if at least one additional coating in the form of a sustained release coating is applied as step f), the step of applying at least one additional coating in the form of a delayed release coating, and wherein the solid dosage form is for oral administration.
[44] Method according to item 43, wherein the delayed release coating comprises at least one component selected from coating materials that disintegrate pH-dependently, coating materials that disintegrate time-dependently, coating materials that disintegrate due to enzymatic triggers in the intestinal environment, and combinations thereof.
[45] Method according to item 44, wherein
 the coating materials that disintegrate pH-dependently are selected from poly vinyl acetate phthalate, cellulose acetate trimellitate, hydroxypropyl methylcellulose phthalate HP-50, HP-55 or HP-55S, cellulose acetate phthalate, acrylic acid copolymer, hydroxypropyl methylcellulose acetate succinate (HPMCAS), poly(methacrylic acid, ethyl acrylate) 1:1 (Eudragit® L100-55, Eudragit® L30D-55), poly (methacrylic acid, methyl methacrylate) 1:1 (Eudragit® L-100, Eudragit® L12.5), poly(methacrylic acid, methyl methacrylate) 1:2 (Eudragit® S-100, Eudragit® S12,5, Eudragit® FS30D), and combinations thereof;
 the coating materials that disintegrate time-dependently are selected from polymethacrylates such as poly (ethyl acrylate, methyl methacrylate, trimethylammonioethyl methacrylate chloride) 1:2:0.2 (e.g. Eudragit® RL 30D, Eudragit® RL100, Eudragit® RL PO, and Eudragit® RL 12.5), poly(ethyl acrylate, methyl methacrylate, trimethylammonioethyl methacrylate chloride) 1:2:0.1 (e.g. Eudragit® RS 30D, Eudragit® RS 100, Eudragit® RS PO, and Eudragit® RS 12.5), or poly(ethylacrylate, methylmethacrylate) 2:1 (e.g. Eudragit® NE 30D, Eudragit® NE 40D, Eudragit® NM 30D), polyvinyl acetate (Kollicoat SR 30D), ethylcellulose, and combinations thereof; and
 the coating materials that disintegrate due to enzymatic triggers in the intestinal environment are selected from chondroitin sulfate, pectin, guar gum, chitosan, Inulin, lactulose, raffinose, stachyose, alginate, dextran, xanthan gum, locust bean gum, arabinogalactan, amylose, amylopectin, pullulan, carrageenan, cyclodextrin, scleroglucan, chitin, curdulan, levan, starch, resistant starch, azo compounds being degraded by azo bonds splitting bacteria, and combinations thereof.
[46] Method according to items 43 to 45, wherein the delayed release coating comprises a combination of at least one coating material that disintegrates pH-dependently and at least one coating material that disintegrates due to enzymatic triggers in the intestinal environment.
[47] Method according to any one of items 43 to 46, wherein the delayed release coating comprises a combination of at least one enteric polymer, preferably poly(methacrylic acid, methyl methacrylate) 1:2, and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably and resistant starch.
[48] Method according to any one of items 43 to 47, wherein the delayed release coating comprises i) an inner coating comprising partially neutralized enteric polymer adjusted to pH 8, preferably partially neutralized poly(methacrylic acid, methyl methacrylate) 1:2 adjusted to pH 8, and containing a buffer salt, and ii) an outer coating comprising a combination of at least one enteric polymer, preferably poly(methacrylic acid, methyl methacrylate) 1:2, and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch.
[49] Method according to any one of items 43 to 48, wherein the at least one component, e.g. the combination of the at least one enteric polymer, preferably poly(methacrylic acid, methyl methacrylate) 1:2, and the at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch, is dispersed in an organic solvent, a mixture of organic solvents or a mixture of at least one organic solvent and water, which is applied to the particles preferably by spray coating, more preferably fluidized-bed spray coating.
[50] Method according item 49, wherein the combination is dispersed in a mixture of at least one organic solvent and water, prepared by mixing a enteric polymer dissolved in an organic solvent with an aqueous re-dispersion of the at least one polysaccharide.
[51] Method according to any one of items 43 to 50, wherein the delayed release coating is applied by spray coating, preferably fluidized-bed spray coating.
[52] Method according to any one of items 43 to 51, comprising a delayed release coating for targeted release of the antibody or functional fragment thereof starting in the ileum, the terminal ileum, the ileocolonic region, the ascending colon, transverse colon or the descending colon.
[53] Method according to any of the preceding items, wherein the fraction of total content of antibody or functional fragment thereof present in the solid dosage form as dimers and other aggregates does not exceed by more than 15%, preferably 10%, more preferably 8%, even more preferably 7%, even more preferably 5%, 3%, 2%, or 1.5%, the fraction of total antibody or functional fragment thereof present as dimers and other aggregates at the time of adding the antibody or functional fragment thereof to the binding liquid.

[54] Method according to any of the preceding items wherein the fraction of total content of antibody or functional fragment thereof present in the solid dosage form as fragments of the full-length antibody or functional fragment thereof does not increase substantially compared to the time of adding the antibody or functional fragment thereof to the binding liquid.

[55] Method according to any of the preceding items wherein the fraction of total content of antibody or functional fragment thereof present in the solid dosage form as fragments of the full-length antibody or functional fragment thereof does not exceed by more than 15%, preferably 10%, more preferably 8%, even more preferably 7%, even more preferably 5%, 3%, 2%, 1.5%, or 1%, the fraction of total content of antibody or functional fragment thereof present as fragments of the full-length antibody or functional fragment thereof at the time of adding the antibody or functional fragment thereof to the binding liquid.

[56] Method according to any of the preceding items, wherein the solid dosage form is an immediate release dosage form, allowing the recovery of at least 80%, preferably at least 85%, more preferably at least 90%, even more preferably at least 93%, even more preferably at least 95%, even more preferably at least 97%, even more preferably at least 98%, of the at least one antibody or functional fragment thereof from the solid dosage form within 2 h, preferably within 1 h, of continuously immersing the solid dosage form in an aqueous buffer solution under constant movement.

[57] Method according to any of the preceding items, wherein the solid dosage form is a sustained release dosage form, allowing the recovery of at least 45%, preferably at least 55%, more preferably at least 65%, even more preferably at least 75%, even more preferably at least 80%, even more preferably at least 85%, even more preferably at least 90%, even more preferably at least 93%, even more preferably at least 95%, even more preferably at least 97%, even more preferably at least 98%, of the at least one antibody or functional fragment thereof from the solid dosage form within 4 h, or 6 h, or 8 h, or 10 h, or 12 h, or 14 h, or 16 h, or 18 h, or 20 h, or 22 h, or 24 h, or 26 h, or 28 h, or 30 h, 32 h, etc., of continuously immersing the solid dosage form in an aqueous buffer solution under constant movement.

[58] Method according to any of the preceding items, wherein the solid dosage form is a sustained release dosage form, allowing a sustained release of the at least one antibody or functional fragment thereof over a time period of at least 5 h, preferably at least 10 h, more preferably at least 12 h, even more preferably at least 20 h, most preferably at least 24 h, upon continuously immersing the solid dosage form in an aqueous buffer solution under constant movement.

[59] Solid dosage form obtainable by the method of any one of items 1 to 58.

[60] Solid dosage form comprising a therapeutically effective dose of at least one antibody or functional fragment thereof, an extrusion-spheronization aid, a surfactant, a buffer, a disintegrant, at least one further excipient selected from the group consisting of fillers, sustained release agents and combinations thereof, and optionally at least one further additive, which is obtainable by the steps of dry mixing, wet granulation, extrusion, spheronization and drying.

[61] Solid dosage form according to item 60, obtainable by the method comprising the steps of dry mixing, wet granulation, extrusion, spheronization and drying as defined in any one of items 1 to 58.

[62] Solid dosage form according to any one of items 59 to 61 for use in the topical treatment of a gastrointestinal disease, preferably an IBD, celiac disease, a gastrointestinal infection, a colorectal cancer or a small intestine cancer, more preferably an IBD.

[63] Solid dosage form for use according to item 62, wherein the IBD is Crohn's disease or ulcerative colitis.

[64] Solid dosage form according to any one of items 59 to 63 for use in the topical treatment in the ileum, the terminal ileum, the ileocolonic region, the ascending colon, transverse colon or the descending colon of a patient.

[65] Multiparticulate drug delivery system, comprising multiple solid dosage form units, each of the solid dosage form unit obtainable by the method of any one of items 1 to 58, wherein the multiparticulate drug delivery system preferably is a sachet, stickpack, drinking straw (Xstraw®), capsule or tablet.

[66] A multiparticulate drug delivery system comprising a plurality of solid dosage form units, each solid dosage form unit comprising at least one antibody or functional fragment thereof, a surfactant, an extrusion-spheronization aid, a buffer, a disintegrant and at least one further excipient selected from the group consisting of fillers, sustained release agents and combinations thereof, and preferably each solid dosage form unit having a predetermined axis and the same predetermined cross-sectional profile, wherein at least 80% by number of those solid dosage form units, preferably 90%, more preferably 95%, have a median aspect ratio between 0.7 and 1.7, the aspect ratio being defined as solid dosage form unit length along the predetermined axis divided by the smallest cross-sectional dimension.

[67] A multiparticulate drug delivery system according to item 66, wherein the median aspect ratio is above 0.8, preferably above 0.9, and below 1.6, preferably below 1.5, more preferably 1.4, even more preferably below 1.3, even more preferably below 1.2, most preferably about 1.

[68] Multiparticulate drug delivery system according to item 66 or 67, wherein the solid dosage form units have a span of aspect ratio of less than 0.9, preferably less than 0.8, more preferably less than 0.7, even more preferably less than 0.6, most preferably less than 0.5.

[69] Multiparticulate drug delivery system according to any of items 66 to 68, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units.

[70] Multiparticulate drug delivery system according to any of items 66 to 69, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units within 30 min, or 1 h, or 2 h, of continuously immersing the solid dosage form in an aqueous buffer solution under constant movement (immediate release).

[71] Multiparticulate drug delivery system according to any of items 66 to 70, allowing the recovery of at least 80%, preferably at least 85%, more preferably at least 93%, even more preferably at least 95%, even more preferably at least 97%, even more preferably at least 98%, of the at least one antibody or functional fragment thereof from the solid dosage form units, within 4 h, or 6 h, or 8 h, or 10 h, or 12 h, or 14 h, or 16 h, or 18 h, or 20 h, or 22 h, or 24 h, or 26 h, or 28 h, or 30 h, or 32 h, or 34 h, or 36 h, etc., of continuously immersing the solid dosage form in an aqueous buffer solution under constant movement (sustained release).

[72] Multiparticulate drug delivery system according to any of items 66 to 71, wherein the solid dosage form units are prepared by extrusion-spheronization.

[73] Multiparticulate drug delivery system according to any of items 66 to 72, wherein the solid dosage form units are prepared by extrusion-spheronization according to the method of any of any one of items 1 to 58.

[74] Multiparticulate drug delivery system according to any of items 66 to 72, wherein the solid dosage form units are prepared by extrusion, and are non-spheronized solid dosage form units.

[75] Multiparticulate drug delivery system according to any of items 66 to 74, wherein the multiparticulate drug delivery system is prepared from multiple solid dosage form units by compression, encapsulation or extrusion-spheronization.

[76] Multiparticulate drug delivery system according to any of items 66 to 75, wherein the multiparticulate drug delivery system or the individual solid dosage form units comprise a delayed release coating, which is applied as a further coating.

[77] A solid dosage form consisting of a single solid dosage form unit of the solid dosage form units comprised in the multparticulate drug delivery system according to any one of items 65 to 76.

DETAILED DESCRIPTION

Figure 1:
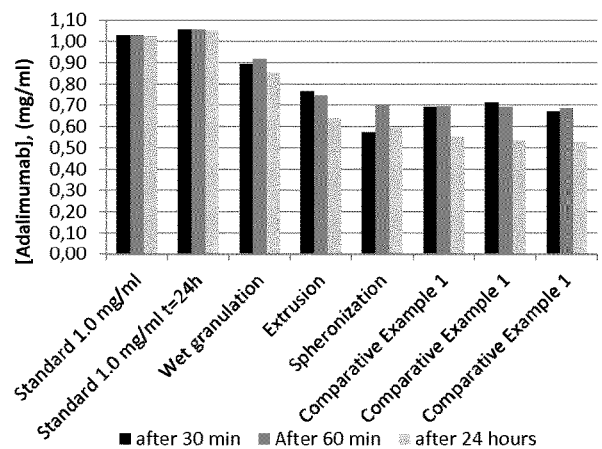
FIG. 1: (A) Adalimumab recovery in citrate-TRIS buffer pH 7, (B) aggregation profile and (C) fragmentation profile of adalimumab after individual steps during the preparation of Comparative Example 1 pellets by wet granulation, extrusion, spheronization and drying in comparison to a 1.0 mg/ml adalimumab standard, determined 30 min, 60 min or 24 h after each step. Adalimumab quantification was determined calorimetrically by total protein content analysis using Bradford reagent.
Figure 1:
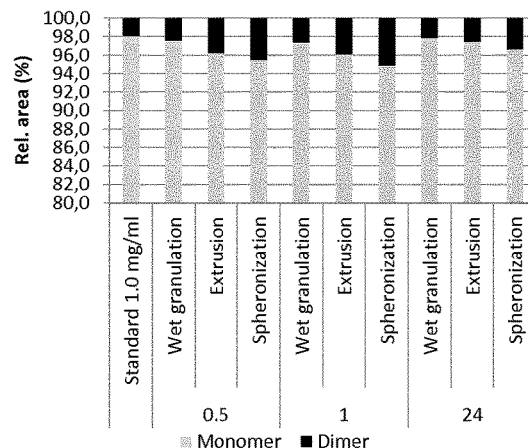
Figure 1:
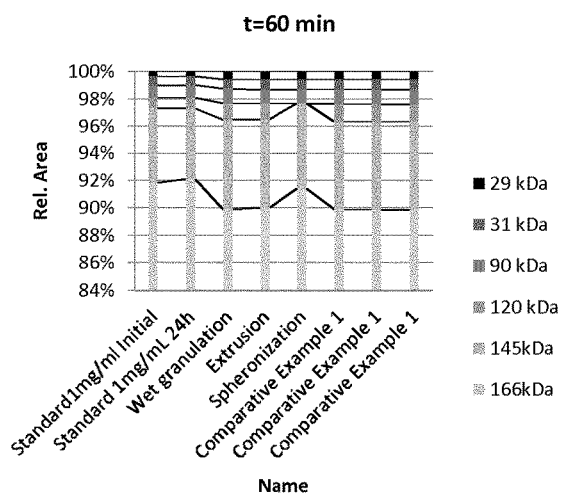
Figure 1:
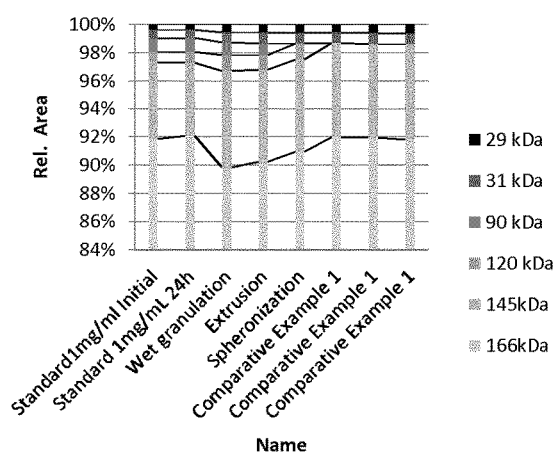

The present invention relates to a method for preparing a solid dosage form comprising at least one antibody or functional fragment thereof, a surfactant, an extrusion-spheronization aid, a buffer, a disintegrant and at least one further excipient selected from the group consisting of fillers, sustained release agents and combinations thereof. In its most general form the inventive method comprises the steps of a) providing a powder blend comprising the extrusion-spheronization aid, the disintegrant, and the at least one further excipient; b) wet granulating by adding a binding liquid to the powder blend of step a) to obtain a wet mass; c) extruding the wet mass of step b) and collecting an extrudate; d) spheronizing the extrudate of step c) to obtain wet spheroids; and e) drying the wet spheroids to obtain the final solid dosage form; wherein the powder blend and/or the binding liquid comprises the at least one antibody or functional fragment thereof, the buffer and the surfactant.

The term "solid dosage form" as used herein may be understood to be equivalent to "solid pharmaceutical dosage form" or "pharmaceutical composition formulated into a solid dosage form" and includes for example pellets, capsules, granules, mini tablets and such. In one embodiment of the present invention the solid dosage form is a pellet, mini sphere, bead, granule or mini tablet. In a preferred embodiment of the present invention, the solid dosage form is a pellet. Multiple unit solid dosage forms of the present invention may be combined into a single-unit formulation, for example in the form of a tablet, hard gelatin/HPMC capsule, sachet/stickpack, drinking straw (Xstraw®), caplet, or pill.

The term "about", as used herein, indicates the value or range of a given quantity can include quantities ranging within 10% of the stated value or range, or optionally within 5% of the value or range, or in some embodiments within 1% of the value or range.

The term "antibody", in the context of the present invention, refers to "immunoglobulin" (Ig), which is defined as a protein belonging to the class IgG, IgM, IgE, IgA, or IgD (or any subclass thereof), and includes all conventionally known antibodies and functional fragments thereof. In the context of the present invention, a "functional fragment" of an antibody/immunoglobulin is defined as antigen-binding fragment or other derivative of a parental antibody that essentially maintains the properties of such a parental antibody. An "antigen-binding fragment" of an antibody/immunoglobulin is defined as a fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. "Antigen-binding fragments" according to the invention include the domain of a F(ab')$_2$ fragment and a Fab fragment. "Functional fragments" of the invention include Fab fragment, F(ab')$_2$ fragment, Fab' fragment, scFv, dsFv, VHH, diabody, triabody, tetrabody, Fc fusion protein and minibody. The F(ab')$_2$ or Fab domain may be engineered to minimize or completely remove the intermolecular disulphide interactions that occur between the CH1 and CL domains. The antibodies or functional fragments used for the present invention may be part of bi- or multifunctional constructs.

Fab fragments can be obtained as the purified digestion products after digestion of an antibody with a cysteine proteinase like papain (EC 3.4.22.2). F(ab')$_2$ fragments can be obtained as the purified digestion products after digestion of an antibody with pepsin (EC 3.4.23.1) or IdeS (Immunoglobulin degrading enzyme from *Streptococcus pyogenes*; EC 3.4.22). Fab' fragments can be obtained from F(ab')$_2$ fragments in mild reducing conditions, whereby each F(ab')$_2$ molecule gives rise to two Fab' fragments. An scFv is a single chain Fv fragment in which the variable light ("$V_L$") and variable heavy ("$V_H$") domains are linked by a peptide bridge.

A "diabody" is a dimer consisting of two fragments, each having variable regions joined together via a linker or the like (hereinafter referred to as diabody-forming fragments), and typically contain two Vls and two VHs. Diabody-forming fragments include those consisting of $V_L$ and $V_H$, $V_L$ and $V_L$, $V_H$ and $V_H$, etc., preferably $V_H$ and $V_L$. In diabody-forming fragments, the linker joining variable regions is not specifically limited, but preferably short enough to avoid noncovalent bonds between variable regions in the same fragment. The length of such a linker can be determined as appropriate by those skilled in the art, but typically 2-14 amino acids, preferably 3-9 amino acids, especially 4-6 amino acids are used. In this case, the $V_L$ and $V_H$ encoded on the same fragment are joined via a linker short enough to avoid noncovalent bonds between the $V_L$ and $V_H$ on the same chain and to avoid the formation of single-chain variable region fragments so that dimers with another fragment can be formed. The dimers can be formed via either covalent or noncovalent bonds or both between diabody-forming fragments.

Moreover, diabody-forming fragments can be joined via a linker or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Based on the same principle as for preparing diabodies, polymerized antibodies such as trimers or tetramers can also be prepared by joining three or more diabody-forming fragments.

In one embodiment, the functional fragment in the solid dosage form prepared by the inventive method is a Fab fragment, a F(ab')2 fragment, a Fab' fragment, an scFv, a dsFv, a VHH, a diabody, a triabody, a tetrabody, an Fc fusion protein or a minibody. Preferred functional fragments used in the present invention are Fab fragments, F(ab')$_2$ fragments, Fab' fragments, scFv and diabodies.

The antibody or functional fragment thereof used in the inventive method for the preparation of the solid dosage form is not particularly limited. In one embodiment, the antibody or functional fragment thereof is an antibody. In another embodiment of the present invention, the antibody or functional fragment thereof is functional fragment as defined above. The antibody or functional fragment thereof may further comprise one or more modifications, e.g. in the form of added or substituted residues, that improve stability, specificity or targeting. These may include any such modifications that are known in the art.

The antigen against which the antibody or functional fragment is directed i.e. the immunogen, peptide, protein, or other molecular structure to which the antibody or functional fragment thereof can specifically bind, is not limited. In its most general form (and when no defined reference is mentioned), "specific to" or "specific binding" refers to the ability of the antibody or functional fragment thereof to discriminate between the target of interest and an unrelated biomolecule (e.g. for antibodies specific to human TNFα to discriminate between human TNFα and an unrelated biomolecule), as determined, for example, in accordance with specificity assay methods known in the art. Such methods comprise, but are not limited to, Western blots and enzyme-linked immunosorbent assay (ELISA) tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment of the present invention the antibody or functional fragment thereof is suitable for use in the treatment of a gastrointestinal disease, for example an inflammatory bowel disease (IBD) (e.g. Crohn's disease or ulcerative colitis), cancer (e.g. colorectal cancer or small intestine cancer), celiac disease, or an infections (e.g. Clostridium difficile infection), more preferably an IBD. In another embodiment of the present invention the antibody or functional fragment thereof is suitable for use in the topical treatment in the jejunum, ileum or large intestine of the gastrointestinal tract of a patient.

In a further embodiment of the present invention the antibody or functional fragment thereof is selected from antibodies specific to tumor necrosis factor alpha (TNFα) and functional fragments thereof, antibodies specific to a4137 integrin and functional fragments thereof, antibodies specific to CD3, CD4 or CD20 and functional fragments thereof, antibodies specific to interleukin 6 (IL-6), interleukin 12 (IL-12), interleukin 13 (IL-13), interleukin 23 (IL-23) or to their receptors and functional fragments thereof, antibodies specific to CXCL10/IP-10 and functional fragments thereof, and antibodies specific to p40 protein subunit and functional fragments thereof. In yet another embodiment of the present invention the antibody or functional fragment thereof is selected from infliximab, adalimumab, etanercept, certolizumab pegol, golimumab, visilizumab, eldelumab, abrilumab, canakinumab, tocilizumab, ustekinumab, natalizumab, etrolizumab, priliximab, vedolizumab and functional fragments thereof.

In one embodiment of the present invention, the antibody or functional fragment thereof in the solid dosage form prepared by the inventive method specifically binds to TNFα. The terms "anti-TNFα antibody", "TNFα antibody" and "antibody specific to TNFα" as used herein are interchangeable. In one embodiment, specific binding refers to the ability of the antibody or fragment to discriminate between human TNFα and human TNFβ. In a preferred embodiment of the present invention the TNFα antibody or functional fragment thereof is a TNFα antibody. In an alternatively preferred embodiment of the present invention the TNFα antibody or functional fragment thereof is a functional fragment of a TNFα antibody.

Several monoclonal antibodies against TNFα have been described in the prior art. Meager et al. (Hybridoma, 6, 305-311, 1987) describe murine monoclonal antibodies against recombinant TNFα. Fendly et al. (Hybridoma, 6, 359-370, 1987) describe the use of murine monoclonal antibodies against recombinant TNFα in defining neutralizing epitopes on TNF. Furthermore, in international patent application WO 92/11383, recombinant antibodies, including CDR-grafted antibodies, specific for TNFα are disclosed. U.S. Pat. No. 5,919,452 discloses anti-TNFα chimeric antibodies and their use in treating pathologies associated with the presence of TNFα. Further anti-TNFα antibodies are disclosed in Stephens et al. (Immunology, 85, 668-674, 1995), GB-A-2 246 570, GB-A-2 297 145, U.S. Pat. No. 8,673,310, US 2014/0193400, EP 2 390 267 B1, U.S. Pat. Nos. 8,293,235, 8,697,074, WO 2009/155723 A2 and WO 2006/131013 A2.

Currently approved anti-TNFα biotherapeutics include (i) infliximab, a chimeric IgG anti-human monoclonal antibody (Remicade®); (ii) etanercept, a TNFR2 dimeric fusion protein, with an IgG1 Fc (Enbrel®); (iii) adalimumab, a fully human monoclonal antibody (mAb) (Humira®), (iv) certolizumab, a PEGylated Fab fragment (Cimzia®) and (v) golimumab, a human IgG1K monoclonal antibody (Simponi®). Moreover, various biosimilars are in development. Therefore, in one embodiment of the present invention, the antibody or functional fragment thereof is selected from infliximab, adalimumab, etanercept, certolizumab pegol and golimumab or functional fragments thereof. In another embodiment of the present invention, the at least one antibody or functional fragment thereof is selected from anti-TNFα antibody or functional fragment thereof as disclosed in PCT applications PCT/EP2017/056218, PCT/EP2017/056246, PCT/EP2017/056237 and PCT/EP2017/056227, as originally filed. In yet another embodiment of the present invention, the at least one antibody or functional fragment thereof is an anti-TNFα antibody or functional fragment thereof with a light chain variable domain and/or a heavy chain variable domain comprising complementarity-determining regions (CDRs) with amino acid sequences as disclosed in PCT applications PCT/EP2017/056218, PCT/EP2017/056246, PCT/EP2017/056237 and PCT/EP2017/056227, as originally filed.

In a preferred embodiment of the present invention, the at least one antibody or functional fragment thereof is selected from anti-TNFα antibodies or functional fragments thereof with a light chain variable domain and/or a heavy chain variable domain comprising one or more CDRs with amino acid sequences as disclosed in SEQ ID NO:7, 9, 12, 14, 24 and 25 of PCT/EP2017/056218, in SEQ ID NO:7-11 and 6 of PCT/EP2017/056246, in SEQ ID NO:7-12 of PCT/EP2017/056237, in SEQ ID NO:1-4, 7 and 6 of PCT/EP2017/056227, and combinations thereof. In another preferred embodiment of the present invention, the at least one antibody or functional fragment thereof is selected from anti-TNFα antibodies or functional fragments thereof with a light chain variable domain and a heavy chain variable domain comprising CDRs with amino acid sequences as disclosed in claim 2 of PCT/EP2017/056218, in claim 2 of PCT/EP2017/056246, in claim 2 of PCT/EP2017/056237 and/or in claim 2 PCT/EP2017/056227, as originally filed. In yet another preferred embodiment of the present invention, the at least one anti-TNFα antibody or functional fragment thereof is selected from the group consisting of anti-TNFα antibodies or functional fragments thereof comprising a heavy chain variable domain amino acid sequence and/or a light chain variable domain amino acid sequence according to claim 4 of PCT/EP2017/056218, claims 5 and 6 of PCT/EP2017/056246, claims 5 and 6 of PCT/EP2017/056237, claim 4 of PCT/EP2017/056227, and combinations thereof.

Surprisingly it has been found by the present inventors that the inclusion of a surfactant in the binding liquid to be added to the powder blend of extrusion-spheronization aid, disintegrant and at least one further excipient, or in the powder blend, drastically improves the recovery of intact antibodies or functional fragments thereof from the solid dosage form upon dissolution of the solid dosage form. Therefore, the solid dosage form prepared by the method of the present invention comprises one or more surfactants. As used herein, the term "surfactant" refers to a surface-active substance, i.e. a substance that reduces the surface tension of a fluid in which it is dissolved and/or reduces the interfacial tension between oil and water. Surfactants can be e.g. ionic or non-ionic. Exemplary non-ionic surfactants that can be included in the solid dosage form prepared by the method of the present invention include but are not limited to polysorbates such as polysorbates 20, 28, 40, 60, 65, 80, 81 and 85; poloxamers such as poloxamers 124, 181, 188, 237, 331, 338 and 407; or polyethylene-polypropylene glycol; alkyl poly(ethylene oxide), alkyl polyglucosides (e.g., octyl glucoside and decyl maltoside); fatty alcohols such as cetyl alcohol and oleyl alcohol; glyceryl monostearate, lecithin, sorbitan monopalmitate, sodium glycolate, sodium de(s)oxycholate, polyethoxylated castor oil (Kolliphor® EL), PEG-40 hydrogenated castor oil (Cremophor® RH40), macrogol 15 hydroxystearate, polyoxyl 15 hydroxystearate (Kolliphor® HS 15), caprylocaproyl macrogol-8 glyceride (Labrasol®), D-α-Tocopherol polyethylene glycol 1000 succinate (vitamin E TPGS). In one embodiment of the inventive method the surfactant is selected from the group consisting of polysorbate 20 (Tween® 20), polysorbate 28, polysorbate 40, polysorbate 60, polysorbate 65, polysorbate 80, polysorbate 81, polysorbate 85, poloxamer 124, poloxamer 181, poloxamer 188 (Kolliphor® 188), poloxamer 237, poloxamer 331, poloxamer 338 and poloxamer 407, glyceryl monostearate, polyethoxylated castor oil (Kolliphor® EL), PEG-40 hydrogenated castor oil (Cremophor® RH40), macrogol 15 hydroxystearate, polyoxyl 15 hydroxystearate (Kolliphor® HS 15), caprylocaproyl macrogol-8 glyceride (Labrasol®), D-α-Tocopherol polyethylene glycol 1000 succinate (vitamin E TPGS), glyceryl monostearate, lecithin, sorbitan monopalmitate, cetyl alcohol, oleyl alcohol, sodium glycolate, sodium de(s)oxycholate, polyethylene glycol, polypropylene glycol, alkyl poly(ethylene oxide), alkyl glycosides, alkyl polyglucoside, octyl glucoside, decyl maltoside. In a preferred embodiment of the inventive method the surfactant is selected from the group consisting of polysorbate 20 (Tween® 20), polysorbate 28, polysorbate 40, polysorbate 60, polysorbate 65, polysorbate 80, polysorbate 81, polysorbate 85, poloxamer 124, poloxamer 181, poloxamer 188 (Kolliphor® 188), poloxamer 237, poloxamer 331, poloxamer 338 and poloxamer 407, glyceryl monostearate, polyethoxylated castor oil (Kolliphor® EL), PEG-40 hydrogenated castor oil (Cremophor® RH40), macrogol 15 hydroxystearate, polyoxyl 15 hydroxystearate (Kolliphor® HS 15), caprylocaproyl macrogol-8 glyceride (Labrasol®), D-α-Tocopherol polyethylene glycol 1000 succinate (vitamin E TPGS), glyceryl monostearate. In another preferred embodiment the surfactant is selected from polysorbate 20 or poloxamer 188, preferably polysorbate 20.

The amount of surfactant to be used is not particularly limited. In one embodiment of the present invention, the amount of surfactant used relative to the total volume of the binding liquid (w/v) is from 0.005 to 2.0%, preferably 0.01 to 1%, more preferably 0.05 to 0.8%, even more preferably 0.05 to 0.5%, even more preferably 0.1 to 0.5, most preferably about 0.1%. The term "total volume of the binding liquid" refers to the total volume of binding liquid added during step b) of the inventive method. The amount of surfactant relative to the total volume of the binding liquid (w/v) may be about 0.03%, about 0.05%, about 0.08%, about 0.1%, about 0.15%, about 0.2%, about 0.25%, about 0.3%, about 0.4%, about 0.5%, about 0.6%, about 0.7%, or about 0.8%. In another embodiment of the present invention, the concentration (w/w) of the surfactant in the solid dosage form is from 0.001 to 1%, preferably from 0.005 to 0.8%, more preferably from 0.005 to 0.5%, even more preferably 0.01% to 0.25%, based on the total weight of the solid dosage form after step e). In yet another embodiment of the present invention, the concentration (w/w) of the surfactant in the solid dosage form depends on the concentration (w/w) of the at least one antibody or functional fragment thereof, such that for a higher concentration of the at least one antibody or functional fragment thereof a higher concentration of surfactant may be used.

The extrusion-spheronization aid used in the inventive method for the preparation of the solid dosage form is not particularly limited. Examples of extrusion-spheronization aids that can be used for the present invention include microcrystalline cellulose, hydroxypropylmethylcellulose (HPMC), hydroxyethylcellulose, cyclodextrin, pectin, pectinic acid, starch, dextrins, carrageenan, glyceryl monostearate, colloidal silica dioxide. In a preferred embodiment of the present invention the extrusion-spheronization aid is microcrystalline cellulose (e.g. Avicel® PH-101).

The disintegrant in the solid dosage form prepared by the method of the present invention is not particularly limited. Examples of the disintegrant include sodium starch glycolate, croscarmellose sodium, cross-linked polyvinylpyrrolidone, soy polysaccharide or cross-linked alginic acid. In a preferred embodiment of the present invention the disintegrant is sodium starch glycolate (e.g. Explotab®).

The solid dosage form prepared by the inventive method further comprises a buffer (buffer salt). Suitable buffers are known in the art. Suitable buffers may be one or more buffers/buffer salts, for example be selected from acetate, citrate, histidine, hydroxymethylaminomethane (TRIS), and phosphate buffers, and the like. In a specific embodiment, the buffer in the solid dosage form prepared by the inventive method is selected from the group consisting of acetate, citrate, TRIS, histidine and phosphate buffers, and combinations thereof. The buffer may be comprised in the binding liquid or may be comprised in the powder blend. Preferably, the buffer is comprised in the binding liquid if the at least one antibody or functional fragment thereof is comprised in the binding liquid, and is comprised in the powder blend if the at least one antibody or functional fragment thereof is comprised in the powder blend.

The at least one further excipient selected from the group consisting of fillers, sustained release agents and combinations thereof in the solid dosage form prepared by the method of the present invention is not particularly limited. Examples of fillers include dextrose, lactose, lactose monohydrate, lactose anhydrous, mannitol, sorbitol, xylitol, (pregelatinized) starch, sucrose, glucose, raffinose, trehalose, dicalcium phosphate, oxides of magnesium or silicon, titanium carbonate, calcium carbonate, magnesium phosphate, porous calcium phosphate or porous magnesium phosphate, propyleneglycol and polyethylene glycol. Additionally examples of fillers are amino acids such as arginine, histidine, glycine, alanine, lysine, proline, leucine, glutamic acid, serine, aspartic acid and asparagine, and salts thereof. Sustained release agents, according the present invention, are preferably selected from the group of sustained release polymers. Examples of sustained release polymers, in accordance with the present invention, include nonionic poly (ethylene oxide) polymers with a molecular weight between 100,000 and 7,000,000, preferably a molecular weight of about 100,000 (e.g. Polyox® N-10NF from Dows Chemicals), HPMC 2208 type with a viscosity at 2 wt.-% in water at 20° C. between 3 and 100000 mPa·s (such as Methocel K3 Premium LV, Methocel K100 Premium LV, Methocel K4M Premium, Methocel K15 Premium, Methocel K100M Premium from Dows Chemicals), preferably between 2,308 and 9,030 mPa·s (e.g. Methocel K4M Premium and Methocel K15M Premium from Dows Chemical), more preferably between 2,663-4,970 mPa·s (e.g. Methocel K4M Premium from Dows Chemicals), chitosan, xanthan gum, guar gum, tragacanth, locust been gum, acacia gum, carbomers, glyceryl (di)behenate (e.g. Compritol® 888 ATO from Gattefosse), glyceryl palmitostearate (such as Precirol® from Gattefosse), ethylcellulose, polyvinyl acetate (Kollicoat® SR 30D) and polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D and Eudragit® NM 30D).

The powder blend in step a) of the method of the present invention may optionally comprise at least one further additive. The term "additive," as used herein, refers to a non-therapeutic agent added to the formulation to provide a desired consistency, viscosity or stabilizing effect. According to one embodiment of the present invention the at least one further additive is selected from pharmaceutically acceptable additives like glidants, plasticizers, lubricants, stabilizers, preservatives, antioxidants, humectants, protective colloids, dyes, permeation enhancers and protease inhibitors.

The inventive method, in its most general form, comprises as first step, step a), providing a powder blend comprising the extrusion-spheronization aid, the disintegrant, and the at least one further excipient selected from the group consisting of fillers, sustained release agents and combinations thereof. The individual components of the powder blend, i.e. the extrusion-spheronization aid, the disintegrant, and the at least one further excipient, as defined above, can be provided as powders or granules. The general properties of said powders or granules, such as grain size, grain size distribution or bulk density etc., suitable for use in the preparation of solid dosage forms by wet granulation, extrusion and spheronization are known by the person skilled in the art. For example commercially available products like Avicel® PH101 (FMC Biopolymer) as extrusion-spheronization aid, EXPLOTAB® (JRS Pharma) as disintegrant and sorbitol (Sigma-Aldrich) as filler, and/or Methocel K4M (Colorcon Limited, UK), or Polyox® N-10NF (The Dow Chemical Company) as sustained release agents in the form of sustained release polymers can be used.

According to one embodiment of the present invention, the at least one antibody or functional fragment thereof, the buffer (buffer salt) and/or the surfactant are added directly to the powder blend. The at least one antibody or functional fragment thereof may be added directly to the powder blend as a powder or as granules. For example, the at least one antibody or functional fragment thereof can be added as a powder comprising particles containing antibodies or functional fragments thereof, e.g. as a lyophilized, spray dried, air dried or vacuum dried powder. Similarly, the surfactant can be added as a powder or granules comprising the surfactant.

The individual components of step a) can be mixed to give rise to the powder blend by a conventional mixing device. Such mixing devices or blenders are known in the art and include for example a double-paddle mixer with blades counter-rotating at different speeds. If the grain sizes of the individual powdered components of step a) need to be further reduced before proceeding to step b), the powders can be grinded during the dry mixing step, with the help of appropriate mixing equipment. In one embodiment the mixing device for the dry mixing is also used for the wet mixing (i.e. wet granulation or wetting) in step b). The dry mixing stage is performed typically for about 10 minutes at 50 rpm of the blades.

In step b) of the inventive method, a binding liquid, is added to the powder blend from step a), preferably slowly and under continuous mixing, to obtain a wet mass. This step is called wet granulating, wet mixing or wetting, and is carried out for a defined period of time, which may vary depending on the amount of material that is to be mixed. The term "wet granulating" as used herein is understood to be equivalent in meaning to "wet mixing" or "wetting".

According to another embodiment of the present invention, the at least one antibody or functional fragment thereof, the buffer and/or the surfactant are comprised in the binding liquid. The manner in which the at least one antibody or functional fragment thereof is introduced into the binding liquid is not particularly limited. For example, the at least one antibody or functional fragment thereof can be added to the binding liquid as a powder comprising particles containing antibodies or functional fragments thereof, e.g. as a lyophilized, spray dried, air dried or vacuum dried powder, and thereby directly reconstitute the antibody or functional fragment thereof in the binding liquid. Alternatively, the at least one antibody or functional fragment thereof can be added already in solution, e.g. as part of a buffered aqueous solution. Similarly, the surfactant may be introduced into the binding liquid as a powder or as granules comprising the surfactant, or as a solution or suspension comprising the surfactant.

The total volume of binding liquid to be added to a defined amount powder blend from step a) is sufficient to produce a wet mass suitable for extrusion. Thus, the total volume of binding liquid to be added to a defined amount powder blend from step a) is high enough to ensure that the wet mass obtained in step b) has sufficient cohesion and plasticity to permit extrusion of the wet mass, but low enough not to exceed the liquid uptake capacity of the powder blend. The total volume of binding liquid to be added to produce a wet mass suitable for extrusion may vary depending on the final composition of the powder blend from step a), and can be determined by those skilled in the art. The required total volume of binding liquid to be added can for example be experimentally determined by measurements of Torque or power consumption of the wet mass.

According to a specific embodiment of the present invention, the powder blend in step a) or the binding liquid of step b) further comprises a binder. Suitable binder to be used in accordance with the present invention are not particularly limited and include for example hydroxypropyl methylcellulose, hydroxypropyl cellulose, methyl cellulose, polyvinylpyrrolidone.

In step c) of the method of the present invention, the wet mass from step b) is extruded, preferably at a controlled speed, while, preferably continuously, collecting an extrudate. Suitable extruders for the purpose of the inventive method are known in the art. Examples of suitable extruders include single screw extruder, twin-screw extruder, screen extruder, RAM extruder. In one embodiment of the present invention the extruder is a single-screw extruder (e.g. Caleva Multi-Lab). Suitable settings for the extruder can be determined by those skilled in the art. In one embodiment of the present invention the extruder includes a die plate with 1 mm diameter and 1 mm depth holes and a screw speed of 50 to 200 rpm, preferably about 150 rpm.

In step d) of the method of the present invention, the extrudate of step c) is fed to a spheronizer and spheronized to obtain individual wet spheroids. The spheronizer and the spheronizer settings are not particularly limited. Examples of suitable spheronizers include the Caleva Multilab and larger scale spheronizers from Caleva and other companies. In one embodiment of the present invention the spheronizer consists of a grooved plate that by rotation breaks the extrudate from step c) into smaller fragments, which, depending on plate design, time, speed and formulation of the extrudate become round. Examples of suitable spheronization settings are for example 5 minutes at 1500 rpm.

In step e) of the method of the present invention, the wet spheroids from step d) are dried to obtain the final solid dosage form. During drying the solvent of the binding liquid is removed. Means to dry wet spheroids after spheronization are known in the art, and include for example a fluidized bed, a drying cabinet or an oven. The drying may further be assisted by vacuum. Activity and stability of antibodies and functional fragments thereof as used for the present invention are very sensitive to external stress like temperature fluctuations and particularly to elevated temperatures. Therefore, in accordance with the method of the present invention the temperature during drying is such as to protect the activity and stability of the antibodies and functional fragments thereof, and at the same time allow efficient drying of the wet spheroids to ensure long-term stability and activity of the at least one antibody or functional fragment thereof in the final solid dosage form prepared by the inventive method.

In one embodiment of the present invention during step e) the drying of the wet spheroids is carried out at a temperature lower than 55° C., preferably lower than 50° C., more preferably lower than 45° C., even more preferably at about 40° C. The period of time over which the wet spheroids are dried is not particularly limited, and depends on the means used to dry the wet spheroids and the targeted residual moisture level of the solid dosage form. In one embodiment of the present invention, the wet spheroids from step d) are dried in a fluidized bed, oven, or drying cabinet drying cabinet for 0.5 to 48 h, preferably 0.5 to 24 h, more preferably 2 to 18 h, even more preferably 4 to 16 h, even more preferably 8 to 14 h.

The wet spheroids may be dried until a sufficiently dry solid dosage form is obtained. The solid dosage form is sufficiently dry, when a large proportion of the solvent used (preferably water) in the binding liquid has been removed by evaporation. In one embodiment of the present invention the solid dosage form is understood to be sufficiently dry, when the residual solvent (preferably water) content of the solid dosage form (i.e. the residual moisture level of the solid dosage form) is less than 20 wt.-%, preferably less than 15 wt.-%, more preferably less than 10 wt.-%, even more preferably less than 8 wt.-%, even more preferably less than 5%, most preferably less than 3 wt.-%, 2 wt.-%, 1 wt.-% or 0.5 wt.-%, relative to the total weight of the solid dosage form.

To preserve activity and stability of the antibody and functional fragment thereof used for the present invention, in accordance with the present invention, the conditions during preparation of the solid dosage form are such as to be conducive to the activity and stability of the antibodies and functional fragments (e.g. by avoiding elevated temperatures, pressures, shear forces, enzymatic contaminations, etc.). Therefore, in one embodiment of the present invention at any time during steps a) to d) the temperature of the antibody or functional fragment thereof is lower than 55° C., preferably lower than 50° C., more preferably lower than 45° C., even more preferably lower than 40° C., even more preferably lower than 35° C., most preferably lower than 30° C. In an alternative embodiment of the present invention at any time during steps a) and e) the temperature of the at least one antibody or functional fragment thereof is lower than the melting temperature (Tm) of the at least one antibody or functional fragment thereof. The above is understood to mean that in case more than one antibody or functional fragment are included the solid dosage form, the temperature is to be lower than the melting temperature (Tm) of the antibody or functional fragment thereof with the lowest Tm. In yet another embodiment of the present invention, wherein after step e), as step f) at least one additional coating in the form of a sustained release coating is applied, the temperature of the solid dosage form comprising the at least one antibody or functional fragment thereof at any time during step f) is lower than the melting temperature (Tm) of the at least one antibody or functional fragment thereof.

In one embodiment of the present invention, the solid dosage form prepared by the method of the present invention is an immediate release dosage form. As used herein, the term "immediate release" is meant to describe those solid dosage forms in which more than 50%, preferably more than 60%, even more preferably more than 70%, etc., of the antibody or functional fragment thereof is released from the solid dosage form within about 2 h, preferably within about 1h, even more preferably within about 0.5 h, of immersion in an aqueous solution. The term an "aqueous solution" as used herein may refer to solution or suspension of which a large part is water (e.g. more than 30 wt.-%, preferably more than 40 wt.-%, preferably more than 50 wt.-%, preferably more than 60 wt.-%, most preferably more than 70 wt.-% of water). This includes intestinal fluid. The term "aqueous buffered solution" refers to an aqueous solution comprising a buffer. The solid dosage form may be an immediate release dosage form after completion of step e) of the inventive method. However, additional coatings that modify the release of the at least one antibody or functional fragment thereof from the solid dosage form, e.g. in the form of a sustained release coating or a delayed release coating, may be applied after completion of step e) in accordance with the present invention.

To measure the amount of antibody or functional fragment released from a solid dosage form in to an aqueous solution, the solid dosage form can be immersed in a defined volume of aqueous solution for a defined period of the time and the resulting concentration of or functional fragment in the aqueous solution can be determine. Means to determine an antibody concentration in an aqueous solution are known in the art and include for example by measuring the absorbance at 280 nm or by using a colorimetric, reagent-based protein assay techniques like Bradford assay or by ELISA. In one embodiment of the present invention, the solid dosage form is an immediate release dosage form after completion of step e), allowing the recovery of at least 80%, preferably at least 85%, more preferably at least 90%, even more preferably at least 92%, even more preferably at least 93%, even more preferably at least 95%, even more preferably at least 97%, even more preferably at least 98%, of the at least one antibody or functional fragment thereof from the solid dosage form within 1 h of continuously immersing the solid dosage form in an aqueous buffer solution under constant movement.

It is to be understood that throughout the present disclosure, whenever referring to dissolution of, or recovery of antibodies or functional fragments thereof from, a solid dosage form/multiparticulate drug delivery system (as in the section just above), e.g. by continuously immersing a solid dosage form/multiparticulate drug delivery system in an aqueous buffered solution under constant movement, for example the following standard testing setup, or a related standard testing setup known to the person skilled in the art, can be used: The release of the at least one antibody or functional fragment thereof can be evaluated using a standard dissolution apparatus I (baskets), II (paddle), III (reciprocating cylinder) or apparatus IV (flow through cell), where the buffer (i.e. aqueous buffered solution) is equilibrated at 37° C. The buffer volume used for dissolution testing can be adapted for instance using mini-vessels in the apparatus I or II to allow reduction of volume required and to be more biorelevant. Release of antibodies or functional fragments thereof during dissolution can be quantified offline by an ELISA method.

If the solid dosage form to be prepared by steps a) to e) of the inventive method is an immediate release solid dosage form, the at least one further excipient to be included in step a) of the inventive method is a substance that enables fast dissolution of the solid dosage form. Further excipients for use in an immediate release solid dosage form prepared by the inventive method are fillers and may include one or more selected from dextrose, lactose, lactose monohydrate, lactose anhydrous, mannitol, sorbitol, xylitol, sucrose, glucose, raffinose, trehalose, dicalcium phosphate, oxides of magnesium or silicon, titanium carbonate, calcium carbonate, magnesium phosphate, porous calcium phosphate or porous magnesium phosphate, amino acids such as arginine, histidine, glycine, alanine, lysine, proline, leucine, glutamic acid, serine, aspartic acid, and asparagine and respective salts thereof, propylene glycol, polyethylene glycol; preferably dextrose, mannitol, sucrose, sorbitol, xylitol, trehalose and dicalcium phosphate, and amino acids such as arginine, histidine, glycine, alanine, lysine, proline, leucine, glutamic acid, serine, aspartic acid and asparagine, and respective salts thereof; more preferably sucrose, trehalose, sorbitol or mannitol, and amino acids such as arginine, histidine, glycine, alanine, lysine, proline, leucine, glutamic acid, serine, aspartic acid and asparagine, and respective salts thereof; even more preferably sorbitol. In a preferred embodiment of the inventive method for the preparation of an immediate release solid dosage form, the powder blend in step a) comprises microcrystalline cellulose as extrusion-spheronization aid; sodium starch glycolate, as disintegrant; and sorbitol or mannitol, preferably sorbitol, as filler.

In another preferred embodiment of the inventive method for the preparation of an immediate release solid dosage form (after completion of step e) of the inventive method), the powder blend in step a) comprises 20 to 90%, preferably 30 to 80%, more preferably 40 to 75%, even more preferably 45 to 70%, most preferably about 45 to 50% extrusion-spheronization aid; 0.5 to 50%, preferably 0.5 to 40, more preferably 1 to 35%, even more preferably 1 to 30%, even more preferably 1 to 15%, most preferably about 1 to 10%, alternatively most preferably 10 to 30%, of the disintegrant; and 2.5 to 55%, preferably 5 to 50%, more preferably 10 to 40%, even more preferably 20 to 40%, most preferably about 30 to 40%, alternatively most preferably 20 to 30%, of a filler (preferably sorbitol, sucrose, trehalose, or mannitol, amino acids such as arginine, histidine, glycine, alanine, lysine, proline, leucine, glutamic acid, serine, aspartic acid and asparagine, and respective salts thereof, and combinations thereof) as the at least one further excipient.

In yet another preferred embodiment of the inventive method for the preparation of an immediate release solid dosage form (after completion of step e) of the inventive method), wherein the powder blend comprises the at least one antibody or functional fragment thereof, the powder blend in step a) comprises 20 to 70%, preferably 30 to 60%, more preferably 40 to 50%, even more preferably about 45%, extrusion-spheronization aid; 0.5 to 30%, preferably 0.5 to 20%, more preferably 1 to 15%, even more preferably 1 to 10%, of the disintegrant; 5 to 50%, preferably 10 to 45%, more preferably 20 to 40%, even more preferably 30 to 40%, of a filler (preferably sucrose, trehalose, sorbitol or mannitol amino acids such as arginine, histidine, glycine, alanine, lysine, proline, leucine, glutamic acid, serine, aspartic acid and asparagine, and respective salts thereof, and combinations thereof) as the at least one further excipient; and 0.1 to 30%, preferably 1 to 25%, more preferably 1 to 20%, even more preferably 2 to 15%, even more preferably 5 to 15%, of the at least one antibody or functional fragment thereof. In another embodiment of the present invention, the solid dosage form prepared by the method of the present invention is a sustained release dosage form. As used herein, the term "sustained release" is used to describe those solid dosage forms, which release a substantial fraction of antibody or functional fragment thereof from the solid dosage form over a prolonged period of time, e.g. over at least 6 h, preferably at least 8h, at least 10 h, at least 12 h, at least 14 h, at least 16 h, at least 18 h, or at least 24 h, etc. In a preferred embodiment of the present invention the solid dosage form is a sustained release dosage form, allowing the recovery of at least 45%, preferably at least 55%, more preferably at least 65%, even more preferably at least 75%, even more preferably at least 80%, even more preferably at least 85%, even more preferably at least 90%, even more preferably at least 93%, even more preferably at least 95%, even more preferably at least 98% of the at least one antibody or functional fragment thereof from the solid dosage form within a defined time period (e.g. 4 h, or 6 h, or 8 h, or 10 h, or 12 h, or 14 h, or 16 h, or 18 h, or 20 h, or 22 h, or 24 h, or 26 h, or 28 h, or 30 h, or 32 h, or 34 h, or 36 h, etc.) of continuously immersing the solid dosage form in an aqueous solution. In another preferred embodiment of the present invention the solid dosage form is a sustained release dosage form, allowing a sustained release of the at least one antibody or functional fragment thereof over a time period of at least 5 h, preferably at least 10 h, more preferably at least 12 h, even more preferably at least 20 h, most preferably at least 24 h, upon continuously immersing the solid dosage form in an aqueous solution. In an alternatively preferred embodiment of the present invention, the solid dosage form is a sustained release dosage form, allowing a sustained release of the at least one antibody or functional fragment thereof over a time period of at least 8 h, at least 10 h, at least 12 h, at least 14 h, or at least 16 h upon continuously immersing the solid dosage form in an aqueous buffer solution under constant movement.

In particular for conditions that affect a section of the gastrointestinal tract, including the ileum and large intestine, such as Crohn's Disease and ulcerative colitis, a sustained release solid dosage form of an active biological agent in the form of an antibody or functional fragment thereof, exhibiting limited systemic absorption can be desirable.

For sustained release solid dosage forms prepared by the method of the present invention at least one further excipient is a sustained release agent, which may be selected from sustained release polymers. However more than one, e.g. two, three or four, sustained release polymers can be included. Sustained release polymers suitable for the present invention include nonionic poly(ethylene oxide) polymers with a molecular weight between 100,000 and 7,000,000, preferably a molecular weight of about 100,000 (e.g. Polyox® N-10NF from Dow Chemicals); HPMC 2208 type with a viscosity at 2 wt.-% in water at 20° C. between 3 and 100000 mPa·s (such as Methocel K3 Premium LV, Methocel K100 Premium LV, Methocel K4M Premium, Methocel K15 Premium, Methocel K100M Premium from Dow Chemicals), preferably between 2,308 and 9,030 mPa·s (e.g. Methocel K4M Premium and Methocel K15M Premium from Dows Chemical), more preferably between 2,663-4,970 mPa·s (e.g. Methocel K4M Premium from Dow Chemicals); chitosan, xanthan gum, guar gum, tragacanth, locust been gum, acacia gum, carbomers, glyceryl (di)behenate (e.g. Compritol® 888 ATO from Gattefosse); glyceryl palmitostearate (such as Precirol®); polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D and Eudragit® NM 30D), ethylcellulose; preferably nonionic poly(ethylene oxide) polymers with a molecular weight of about 100,000 (Polyox® N-10NF); HPMC 2208 type with a viscosity at 2% in water at 20° C. of 2,663-4,970 mPa·s (Methocel K4M, Dow Chemicals); and glyceryl (di) behenate (Compritol® 888 ATO).

In a preferred embodiment of the inventive method for the preparation of a sustained release solid dosage form, the powder blend in step a) comprises microcrystalline cellulose as extrusion-spheronization aid; sodium starch glycolate, as disintegrant; and Polyox® N-10NF or Methocel K4M as the at least one further excipient. In another preferred embodiment of the inventive method for the preparation of a sustained release solid dosage form, the powder blend in step a) comprises 20 to 90%, preferably 45 to 80%, more preferably 50 to 80%, even more preferably 60 to 75%, most preferably about 70 to 75% extrusion-spheronization aid; 0.1 to 45%, preferably 0.5 to 35%, more preferably 1 to 30%, even more preferably 1 to 25%, even more preferably 1 or 15%, most preferably about 5 to 15% of the disintegrant; and 0.5 to 30%, preferably 1 to 20%, more preferably 2.5 to 12.5%, even more preferably 2.5 to 10%, most preferably about 2.5 to 7.5%, of the at least one further excipient comprising at least one sustained release agent.

In an alternatively preferred embodiment of the inventive method for the preparation of a sustained release solid dosage form, at least two further excipients are added in step a), wherein the first further excipient is a sustained release agent, preferably a sustained release polymer, and the second further excipient is a filler, preferably sucrose, trehalose, sorbitol or mannitol, amino acids such as arginine, histidine, glycine, alanine, lysine, proline, leucine, glutamic acid, serine, aspartic acid and asparagine, and respective salts thereof, and combinations thereof, more preferably sorbitol. If at least two further excipients are added in step a), the powder blend in step a) may comprise 20 to 90%, preferably 45 to 85%, more preferably 50 to 80%, even more preferably 60 to 80%, most preferably about 75% extrusion-spheronization aid; 0.1 to 40%, preferably 0.5 to 30%, more preferably 1 to 20%, even more preferably 1 to 15%, most preferably 1 to 10% of the disintegrant; 1 to 30%, preferably 1 to 20%, more preferably 2.5 to 12.5%, even more preferably 2.5 to 10%, most preferably about 2.5 to 7.5%, of the sustained release agent; and 0.5 to 30%, preferably 1 to 20%, more preferably 1 to 15%, even more preferably 5 to 15%, most preferably about 10% of the filler.

In another embodiment of the inventive method for the preparation of a sustained release solid dosage form, the powder blend in step a) comprises microcrystalline cellulose as extrusion-spheronization aid; glyceryl (di)behenate as first further excipient; and a filler, preferably sorbitol, sucrose, trehalose, or mannitol, or amino acids such as arginine, histidine, glycine, alanine, lysine, proline, leucine, glutamic acid, serine, aspartic acid and asparagine, and respective salts thereof, and combinations thereof, as second further excipient.

In yet another embodiment of the inventive method for the preparation of an sustained release solid dosage form, the powder blend in step a) comprises 30 to 85%, preferably 45 to 80%, more preferably 50 to 80%, even more preferably about 75% extrusion-spheronization aid; 1 to 35%, preferably 1 to 25%, more preferably 2.5 to 15%, even more preferably about 2.5 to 10%, of glyceryl (di)behenate as the first further excipient; 2.5 to 45%, preferably 5 to 40%, more preferably 10 to 35%, even more preferably 10 to 25%, of the second further excipient in the form of a filler, preferably sucrose, trehalose, sorbitol or mannitol, more preferably sorbitol.

The binding liquid of step b) of the method of the present invention is not particularly limited, as long as it ensures the stability and activity of the antibody or functional fragment thereof and allows its use as a wetting solution for the powder blend of step a) that is at least in part absorbed by the powder blend. Thus, the binding liquid can be any solvent or mixture of solvents that fulfill these criteria. In one embodiment of the present invention the binding liquid is an aqueous solution. In a further embodiment the binding liquid comprises at least one buffer to further ensure the stability of the antibody or functional fragment thereof.

Suitable buffers for use in combination with antibodies or functional fragments thereof are known in the art and include acetate, citrate, histidine, TRIS, and phosphate buffers.

The binding liquid may furthermore comprise a stabilizer. Preferably, when the binding liquid comprises a stabilizer, also the antibody or functional fragment thereof is comprised in the binding liquid. Suitable stabilizers for use in combination with antibodies or functional fragments thereof are known in the art and include polyols (sorbitol, mannitol, glycerol, propyleneglycol, polyethyleneglycol), sugars (sucrose, trehalose, glucose, raffinose), cyclodextrins, and amino acids such as arginine, histidine, glycine, alanine, lysine, proline, leucine, glutamic acid, serine, aspartic acid and asparagine, and respective salts thereof.

The concentration of the at least one antibody or functional fragment thereof in the binding liquid or in the powder blend is not particularly limited. In one embodiment of the present invention, the concentration of the at least one antibody or functional fragment thereof in the binding liquid or in the powder blend is such as to result in an amount of antibody or functional fragment thereof in the solid dosage form prepared by the method of the present invention that allows the administration of a therapeutically effective dose of the at least one antibody or functional fragment thereof as a single unit dose, for example in the form of a tablet, capsule, drinking straw (Xstraw®), or sachet/stickpack comprising multiple solid dosage forms (e.g. in the form of multiple pellets, beads or granules). The term "administration" relates to the manner and form in which the composition comes into first contact with the body of a patient. The solid dosage form prepared by the inventive method can be administered orally, rectally or in any other way that results in the accumulation of the solid dosage form at the intended site of local application and/or absorption into body tissue. Preferably the solid dosage form of the present invention is intended for oral administration. A "therapeutically effective dose" is the amount of the at least one antibody or functional fragment thereof required to provide the desired therapeutic effect. The exact amount may vary for different antibodies or functional fragments thereof and/or for individual patients, but can be determined by one skilled in the art.

In another embodiment of the present invention, the concentration of the antibody in the binding liquid or in the powder blend is such to result in an amount of antibody or functional fragment thereof in the solid dosage form between 0.01 and 60%, preferably 0.05 to 45%, more preferably 0.1 to 30%, even more preferably 0.5 to 25%, even more preferably 1 to 20%, even more preferably 1 to 15%, even more preferably 2 to 15%, most preferably 5 to 15%, relative to the total weight of the solid dosage form after step e). In a further embodiment of the present invention, the at least one antibody or functional fragment thereof is comprised in the binding liquid in a concentration (w/v) of 0.01 to 1000 mg/ml, preferably 0.1 to 500 mg/ml, more preferably 1 to 200 mg/ml, even more preferably 5 to 100 mg/ml, even more preferably 10 to 50 mg/ml. In accordance with the present invention, if the at least one antibody or functional fragment thereof is comprised in the binging liquid, the amount or concentration of antibody or functional fragment thereof in the binding liquid needs to be adjusted depending on the total volume of binding liquid to be added to a defined amount and composition of powder blend from step a), in order to realize a desired loading of antibody or functional fragment thereof relative to the total weight of the final solid dosage form. In a further embodiment of the present invention, the at least one antibody or functional fragment thereof is comprised in the powder blend in a concentration (w/w) of 0.01 to 60%, preferably 0.05 to 45%, more preferably 0.1 to 30%, even more preferably 0.5 to 25%, even more preferably 1 to 20%, even more preferably 1 to 15%.

The amount of the antibody or functional fragment thereof in the solid dosage form prepared by the inventive method will vary according to the pharmacological activity of the antibody or functional fragment, the indication to be treated, the targeted dosing regimen, the projected method of administration, the integrity, stability and dissolution behavior of the final composition and other similar reasons. In one embodiment the amount of the at least one antibody or functional fragment thereof is at least 0.01%, preferably at least 0.05%, more preferably at least 0.1%, even more preferably at least 1%, most preferably at least 2%, relative to the total weight of the solid dosage form, preferably after step e) of the inventive method. In a further embodiment the he amount of the antibody or functional fragment thereof is generally up to 60%, preferably up to 45%, more preferably at least 35%, even more preferably up to 30%, even more preferably up to 25%, even more preferably up to 20%, relative to the total weight of the solid dosage form, preferably after step e) of the inventive method.

If the solid dosage form, prepared according to steps a) to e) of the inventive as described above, is an immediate release dosage form, as step f) at least one additional coating in the form of a sustained release coating may be applied after step e). The manner in which the sustained release coating is applied is not particularly limited, as long as it does not affect the stability and activity of the at least one antibody or functional fragment thereof in the solid dosage form. Methods for applying sustained release coatings are known in the art. In one embodiment of the present invention the delayed release coating is applied by spray coating, for example using fluidized-bed spray coating. The sustained release coating may for example be applied as a coating liquid, e.g. in the form of an aqueous suspension (dispersion) or organic solution comprising sustained release coating materials and optional further excipients, such as plasticizers, anti-tacking excipients and coalescence enhancers.

Sustained release coating materials for the sustained release coating of a solid dosage form in step f) are known in the art. Suitable coating materials for use in a sustained release coating are sustained release polymers, such as polymethacrylates such as poly(ethyl acrylate, methyl methacrylate, trimethylammonioethyl methacrylate chloride) 1:2:0.1 (e.g. Eudragit® RS 100, Eudragit® RS PO, Eudragit® RS 30D and Eudragit® RS 12.5), poly(ethyl acrylate, methyl methacrylate, trimethylammonioethyl methacrylate chloride) 1:2:0.2 (e.g. Eudragit® RL100, Eudragit® RL PO, Eudragit® RL 30D and Eudragit® RL 12.5), or poly(ethylacrylate, methylmethacrylate) 2:1 (e.g. Eudragit® NE 30D, Eudragit® NE 40D and Eudragit® NM 30D), ethylcellulose, polyvinyl acetate (e.g. Kollicoat® SR 30D), and combinations thereof. Sustained release polymers for use in the sustained release coating may be provided as solids, e.g. in the form of a powder or granules, or as suspensions (dispersion), e.g. an aqueous suspension. Preferably the sustained release polymer is provided as a suspension. Optional further excipients for use in the sustained release coating are known to the person skilled in the art, and comprise plasticizers, anti-tacking agents, coalescence enhancer, glidants, antioxidants, humectants, protective colloids, dyes and fillers.

The inventive method allows the activity and stability of the at least one antibody or functional fragment thereof to be preserved in the solid dosage form prepared according to the inventive method. The stability and activity of an antibody or fragment thereof can be estimated for example by determining the fraction of an antibody or functional fragment thereof present as dimers and other aggregates. According to one embodiment of the present invention, the fraction of total content of antibody or functional fragment thereof present in the solid dosage form as dimers and other aggregates does not exceed by more than 15%, preferably 10%, more preferably 8%, even more preferably 7%, even more preferably 5%, 3%, 2%, or 1.5%, the fraction of total antibody or functional fragment thereof present as dimers and other aggregates at the time of adding the antibody or functional fragment thereof to the binding liquid. Methods to determine the fraction of a polypeptide present as dimers and other aggregates are known in the art, and include for example Size Exclusion Chromatography (SEC).

The stability and activity of an antibody or functional fragment thereof can also be estimated for example by determining the fraction of an antibody or functional fragment thereof present as fragments of the full-length antibody or functional fragment thereof. Therefore, in another embodiment of the present invention, the fraction of total content of antibody or functional fragment thereof present in the solid dosage form as fragments of the full-length antibody or functional fragment thereof does not increase substantially compared to the time of adding the antibody or functional fragment thereof to the binding liquid. In a further embodiment of the present invention, the fraction of total content of antibody or functional fragment thereof present in the solid dosage form as fragments of the full-length antibody or fragment thereof does not exceed by more than 15%, preferably 10%, more preferably 8%, even more preferably 7%, even more preferably 5%, 3%, 2%, 1.5%, or 1%, the fraction of total content of antibody or functional fragment thereof present as fragments of the full-length antibody or functional fragment thereof at the time of adding the antibody or functional fragment thereof to the binding liquid. Methods to determine the fraction of an antibody or functional fragment thereof present as fragments of the full-length antibody or functional fragment thereof are known in the art, and include for example microchip electrophoresis analysis.

In one embodiment of the present invention the antibody or functional fragment thereof is suitable for use in the topical treatment in the gastrointestinal tract of a patient. The term "topical treatment" in the context of the present invention, is used to describe the local application of the solid dosage form, as opposed to the systemic application of a dosage form comprising antibodies or functional fragments thereof, e.g. by infusion, injection or implantation. The term "gastrointestinal tract" as used herein describes the system of organs of the human body, that includes all structures between mouth and anus, forming a continuous passage, and is responsible for digesting ingested material, absorbing nutrients and expelling faeces. The term "patient" as used herein refers to a living organism suffering from or prone to a condition that can be treated or prevented by the administration of the at least one antibody or functional fragment thereof. In a preferred embodiment, the patient is a human.

A solid dosage form enables once-daily, several times a day, once-in-two days, etc. delivery of the above classes of antibodies and functional fragments thereof. The topical treatment in the gastrointestinal tract, e.g. the ileum or the large intestine, allows for specific targeting of the gastrointestinal wall, for enhanced treatment of diseases of the ileum and large intestine, by providing high local concentration of antibody or functional fragment thereof, while minimizing side effects that occur because of release of drugs in the upper gastrointestinal tract or unnecessary systemic absorption.

Therefore in another embodiment of the present invention the solid dosage form prepared by the inventive method is for use in the treatment of a disease in the gastrointestinal tract, preferably in the ileum and the large intestine. Such diseases include e.g. IBD, cancer (such as colorectal cancer or small intestine cancer), celiac disease, infections (such as Clostridium difficile infection) of the small intestine and the colon and diarrhea. In a preferred embodiment of the present invention the solid dosage form prepared by the inventive method is for use in the treatment of IBD, e.g. Crohn's disease or ulcerative colitis.

In one embodiment of the present invention, the solid dosage form prepared by the method of the present invention is for oral or rectal, preferably oral, administration. "Oral administration" in context of the present invention means the introduction of the solid dosage form into gastrointestinal tract via the mouth. "Rectal administration" in context of the present invention means the introduction of the solid dosage form into gastrointestinal tract via the anus.

According to one embodiment of the present invention at least one additional coating in the form of a delayed release coating is applied to the solid dosage form after drying in step e), or after step f) if at least one additional coating in the form of a sustained release coating is applied as step f). A delayed release coating within the meaning of the present invention is a coating that prevents the release of the at least one antibody or functional fragment thereof from the solid dosage form, until a specific event, e.g. in the form of a chemical or enzymatic trigger or the lapse of a defined amount of time immersed in solution, occurs.

In a preferred embodiment, the solid dosage form prepared by the method of the present invention is for oral administration, in the form of a pellet, bead, mini sphere, mini tablet, or granule coated with a delayed release coating that prevents the release of the composition for example before the jejunum or before the ileum of the small intestine, preferably before the terminal ileum, more preferably before the ileocolonic region, alternatively before the ascending colon, before the transverse colon or before the descending colon, of the gastrointestinal tract. The ileocolonic region is the region of the gastrointestinal tract where the small intestine merges with the large intestine. The large intestine is the penultimate section of the gastrointestinal tract and can be further subdivided into cecum, colon and rectum. The colon is further subdivided into ascending, transverse and descending colon. The terminal ileum is the penultimate section of the small intestine and is directly adjacent to the cecum.

The manner in which the delayed release coating is applied is not particularly limited, as long as it does not affect the stability and activity of the at least one antibody or functional fragment thereof in the solid dosage form. Methods for applying delayed release coatings are known in the art. In one embodiment of the present invention the delayed release coating is applied by spray coating, preferably fluidized-bed spray coating.

Coating materials for the delayed release of a solid dosage form, in particular for targeted release in the jejunum, the ileum or the large intestine, upon oral administration are known in the art. They can be subdivided into coating materials that disintegrate above a specific pH, coating materials that disintegrate after a specific residence time in the gastrointestinal tract and coating materials that disintegrate due enzymatic triggers specific to the microflora of a specific region of the intestines. Coating materials of these three different categories for targeting to the large intestine have been reviewed for example in Bansal et al. (Polim. Med. 2014, 44, 2, 109-118). These uses of such coating materials have also been described for example in WO2007/122374A2, WO0176562A1, WO03068196A1 and GB2367002A. In one embodiment of the present invention the delayed release coating comprises at least one component selected from coating materials that disintegrate pH-dependently, coating materials that disintegrate time-dependently, coating materials that disintegrate due to enzymatic triggers in the large intestinal environment, and combinations thereof.

Preferred coating materials among coating materials that disintegrate pH-dependently are selected from poly vinyl acetate phthalate, cellulose acetate trimellitate, hydroxypropyl methylcellulose phthalate HP-50, HP-55 or HP-55S, cellulose acetate phthalate, hydroxypropyl methylcellulose acetate succinate (HPMCAS), poly(methacrylic acid, ethyl acrylate) 1:1 (Eudragit® L100-55, Eudragit® L30D-55), poly(methacrylic acid, methyl methacrylate) 1:1 (Eudragit® L-100, Eudragit® L12.5), poly(methacrylic acid, methyl methacrylate) 1:2 (Eudragit® S-100, Eudragit® S12.5, Eudragit® FS30D), and combinations thereof. Preferred coating materials that disintegrate time-dependently are selected from polymethacrylates such as poly(ethyl acrylate, methyl methacrylate, trimethylammonioethyl methacrylate chloride) 1:2:0.2 (e.g. Eudragit® RL 30D, Eudragit® RL100, Eudragit® RL PO, and Eudragit® RL 12.5), poly (ethyl acrylate, methyl methacrylate, trimethylammonioethyl methacrylate chloride) 1:2:0.1 (e.g. Eudragit® RS 30D, Eudragit® RS 100, Eudragit® RS PO, and Eudragit® RS 12.5), or poly(ethylacrylate, methylmethacrylate) 2:1 (e.g. Eudragit® NE 30D, Eudragit® NE 40D, Eudragit® NM 30D), polyvinyl acetate (Kollicoat® SR 30D), ethylcellulose, and combinations thereof. Preferred coating materials among coating materials that disintegrate due to enzymatic triggers in the intestinal environment are selected from chondroitin sulfate, pectin, guar gum, chitosan, inulin, lactulose, raffinose, stachyose, alginate, dextran, xanthan gum, locust bean gum, arabinogalactan, amylose, amylopectin, pullulan, carrageenan, cyclodextrin, scleroglucan, chitin, curdulan, levan, starch, resistant starch, azo compounds being degraded by azo bonds splitting bacteria, and combinations thereof.

In one embodiment of the present invention the coating material for the delayed release coating comprises one, two, three, etc., component(s) selected from the coating materials that disintegrate pH-dependently, the coating materials that disintegrate time-dependently, and the coating materials that disintegrate due to enzymatic triggers in the intestinal environment, listed above, and combinations thereof. In another embodiment of the present invention, the delayed release coating comprises a combination of at least one coating material that disintegrates pH-dependently and at least one coating material that disintegrates due to enzymatic triggers in the intestinal environment.

For example, a delayed release coating can be designed to focus the delivery of the antibody or functional fragment thereof entirely in the large intestine, beginning at the cecum, and continuing through the ascending, transverse, and descending colon, and ending in the sigmoid colon. Alternatively, for example, a delayed release coating can be designed to begin the delivery of the antibody or functional fragment thereof in the jejunum and end the release in the transverse colon. The possibilities and combinations are numerous.

In one embodiment of the present invention, the delayed release coating comprises a combination of at least one pH sensitive (enteric) polymer, e.g. poly(methacrylic acid, methyl methacrylate) 1:2, and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof. In a preferred embodiment of the present invention, the delayed release coating is a combination of poly(methacrylic acid, methyl methacrylate) 1:2 and resistant starch (e.g. Phloral® technology). The delayed release coating comprising at least one enteric polymer, e.g. poly(methacrylic acid, methyl methacrylate) 1:2, and at least one polysaccharide, e.g. resistant starch, may be dispersed in an organic solvent, a mixture of organic solvents or a mixture of at least one organic solvent and water, and then applied to the solid dosage form e.g. by fluidized-bed spray coating.

In another embodiment, the delayed release coating comprises i) an inner coating comprising partially neutralized enteric polymers adjusted to pH 8 (preferably poly(methacrylic acid, methyl methacrylate) 1:2 adjusted to pH 8) and containing a buffer salt, and ii) an outer coating comprising a combination of at least one enteric polymer (preferably poly (methacrylic acid, methyl methacrylate) 1:2) and at least one polysaccharide selected from chondroitin sulfate, cyclodextrin, chitosan, dextran, arabinogalactan, amylose, pullulan, carrageenan, scleroglucan, chitin, curdulan, levan, amylopectin, starch, resistant starch, and combinations thereof, preferably resistant starch. Other preferred embodiments for the delayed release coating can be found among the embodiments disclosed in WO2007122374A2. The above described delayed release coatings optionally comprise at least one excipients listed in one of the embodiments above (e.g. surfactants, fillers, or further additives).

According to a further aspect of the inventive method, in a further step a sachet/stickpack, capsule (e.g. a hard or soft gelatin capsule), HPMC capsule, drinking straw (e.g. Xstraw® from Harro Hofliger) or tablet is provided (multiparticulate drug delivery system) comprising multiple solid dosage forms prepared by the inventive method according to one of the embodiments described above. How to prepare sachets/stickpacks, capsules, drinking straws or tablets comprising multiple solid dosage forms is known in the art. The multiparticulate drug delivery system (e.g. a sachet/stickpack, capsule, drinking straw or tablet) may comprise a total amount of the at least one antibody or functional fragment thereof suitable for oral administration to a human patient. In another embodiment, the sachet/stickpacks, capsule, drinking straws or tablets comprises a therapeutically effective dose of the at least one antibody or functional fragment thereof suitable for oral administration to a human patient.

In an alternative embodiment of the present invention, multiple solid dosage forms prepared by steps a) to d) or steps a) to f) of the inventive method, as described in one of the inventive embodiments above, may be combined into a multiparticulate drug delivery system, e.g. a tablet or capsule. How to prepare such tablets or capsules comprising multiple units is known in the art. The thus prepared tablet or capsule may then be coated with a delayed release coating as described above.

In addition to a method for preparing a solid dosage form as described in the embodiments above, the present invention further relates to solid dosage forms prepared by the method of the present invention as defined by any one of the embodiments described above. The inventive solid dosage forms may be in the form of pellets, beads, mini spheres, granules or mini tablets. The present invention also relates to a multiparticulate drug delivery system in the form of a sachet/stickpack, capsule, drinking straw (Xstraw®), or tablet comprising multiple unit solid dosage forms prepared by the inventive method described above. Furthermore, the present invention relates to said solid dosage forms/multiparticulate drug delivery systems for use in the treatment of a gastrointestinal disease, preferably IBD, colorectal cancer, small intestine cancer, celiac disease or gastrointestinal infections (e.g. Clostridium difficile infection), more preferably IBD, e.g. Crohn's disease or ulcerative colitis, more preferably Crohn's disease or ulcerative colitis. The present invention also relates to solid dosage forms/multiparticulate drug delivery systems prepared by the inventive method described above for use in the topical treatment in the gastrointestinal tract of a patient. Finally the present invention relates said inventive solid dosage forms/multiparticulate drug delivery systems for use in the treatment of a patient suffering from a gastrointestinal disease, preferably IBD, colorectal cancer, small intestine cancer, celiac disease or gastrointestinal infections, more preferably IBD.

In further aspect the present invention relates to a multiparticulate drug delivery system comprising a plurality of solid dosage form units (i.e. single solid dosage forms), each solid dosage form unit comprising at least one antibody or functional fragment thereof, a surfactant, an extrusion-spheronization aid, a buffer (buffer salt), a disintegrant and at least one further excipient selected from the group consisting of fillers, sustained release agents and combinations thereof, and optional further additives, and preferably each solid dosage form unit having a predetermined axis and the same predetermined cross-sectional profile, wherein at least 80% by number of those solid dosage form units, preferably 90%, more preferably 95%, have a median aspect ratio between 0.7 and 1.7, the aspect ratio being defined as solid dosage form unit length along the predetermined axis divided by the smallest cross-sectional dimension.

According to one embodiment of the multiparticulate drug delivery system of the present invention, the median aspect ratio is above 0.8, preferably above 0.9, and below 1.6, preferably below 1.5, more preferably 1.4, even more preferably below 1.3, even more preferably below 1.2, most preferably about 1. According to another embodiment of the multiparticulate drug delivery system of the present invention, the solid dosage form units have a span of aspect ratio less than 0.9, preferably less than 0.8, more preferably less than 0.7, even more preferably less than 0.6, most preferably less than 0.5. For further details regarding aspect ratio, predetermined axis, predetermined cross-sectional profile and span (including definitions and embodiments), it is referred to disclosure of EP 2 512 453. It is to be understood that the above definitions and embodiments regarding aspect ratio and span of the solid dosage form units equally apply to the inventive solid dosage forms according to any one of the embodiments above and to the solid dosage forms prepared by any one of the embodiments of the inventive method described above.

According to a further embodiment of the present invention, the multiparticulate drug delivery system of the present invention, allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units. According to yet another embodiment of the present invention, the multiparticulate drug delivery system of the present invention allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units within 30 min, or 1 h, or 2 h, of continuously immersing the solid dosage form in an aqueous buffer solution under constant movement (immediate release). According to yet another embodiment of the present invention, the multiparticulate drug delivery system of the present invention allows the recovery of at least 80%, preferably at least 85%, more preferably at least 93%, even more preferably at least 95%, even more preferably at least 97%, even more preferably at least 98%, of the at least one antibody or functional fragment thereof from the solid dosage form units within 4 h, or 6 h, or 8 h, or 10 h, or 12 h, or 14 h, or 16 h, or 18 h, or 20 h, or 22 h, or 24 h, or 26 h, or 28 h, or 30 h, or 32 h, or 34 h, or 36 h, etc., of continuously immersing the solid dosage form in an aqueous buffer solution under constant movement (sustained release).

In one embodiment, the solid dosage form units comprised in the multiparticulate drug delivery system are prepared by extrusion-spheronization. According to a specific embodiment of the present invention, the solid dosage form units comprised in the multiparticulate drug delivery system are solid dosage forms prepared by extrusion-spheronization according to the method of any of the embodiments described above. In an alternative embodiment of the present invention, the solid dosage form units comprised in the multiparticulate drug delivery system are prepared by extrusion, and are non-spheronized solid dosage form units. In a further embodiment the multiparticulate drug delivery system is prepared from multiple solid dosage form units by compression, encapsulation or extrusion-spheronization and/or has the properties as defined in any of the embodiments described above relating to multiparticulate drug delivery systems and the method for the preparation thereof.

In a further embodiment of the present invention, the multiparticulate drug delivery system or the individual solid dosage form units comprise a delayed release coating, which is applied as a further coating. Further embodiments for the multiparticulate drug delivery system may be found in EP 2 512 453 and are applicable to the present invention independent of whether these embodiments are disclosed in EP 2 512 453 as referring to spheronized or non-spheronized solid dosage forms.

EXAMPLES

Materials and Methods Applied in the Examples

Citrate-TRIS buffer pH 7 preparation: A solution of sodium citrate 100 mM (2.942 g and completed to 100.0 mL with purified water) was prepared. A solution of citric acid 100 mM (3.842 g dissolved and diluted to 200.0 ml with purified water) was prepared. The pH of the citric acid solution was adjusted to 3.5 with the sodium citrate solution. A TRIS solution 1M (12.114 g and completed to 100.0 ml with purified water) was prepared. The pH of the citrate buffer was adjusted to pH 7.0 with the TRIS solution.

Preparation of Pellets
  Dry mixing: The excipients required for each batch (batch size: 10 g) were mixed using the Mixer attachment (double-paddle mixer) from the Caleva Multilab equipment for about 5 minutes predetermined period of time at 50 rpm.
  Wet mixing: After the dry mixing step, the binding liquid (either deionized water, citrate-TRIS buffer pH 7 or adalimumab solution, including or not a predetermined surfactant concentration) was slowly added to the powder blend of excipients under mixing and mixed for a predetermined period of time and speed.
  Extrusion: The wet mass was then emptied from the mixer and extruded through 1 mm diameter and 1 mm depth holes of the extrusion die using a screw extruder at a constant speed (150 rpm) until all wet mass is extruded.
  Spheronization: The wet extrudate was then fed to the spheronizer attachment, consisting of a grooved plate, which by rotation breaks the wet extrudates into smaller fragments that depending on time, speed and the nature of the individual components of the extrudate become then round (wet spheroids). The extrudate was spheronized for a predetermined amount of time at a given speed.

| Identification in patent application | Wet granulation speed (rpm)/time (min) | Spheronization speed (rpm)/time (min) |
|---|---|---|
| Comparative Example 1 | | |
| Comparative Example 2 | 150/6 | 1500/3 |
| Comparative Example 3 | 150/5 | 1500/3 |
| Example 1 | 150/5 | 1500/3 |
| Example 2 | 150/5 | 1500/3 |
| Example 3 | 150/5 | 1500/3 |
| Example 4 | 150/5 | 1500/3 |
| Example 5 | 150/5 | 1500/3 |
| Example 6 | 150/5 | 1500/30 |
| Example 7 | 150/5 | 1500/6 |
| Example 8 | 150/5 | 1500/6 |
| Example 9 | 50/10 | 1500/6 |
| Example 10 | 50/10 | 1500/10 |
| Example 11 | 50/10 | 1500/6 |
| Example 12 | 50/10 | 1500/10 |
| Example 13 | 50/10 | 1500/12 |
| Example 14 | 50/10 | 1500/8 |
| Comparative Example 4 | 50/15 | 1500/3 |
| Example 15 | 50/10 | 1500/30 |
| Example 16 | 50/10 | 1500/30 |
| Comparative Example 5 | 50/10 | 1500/10 |
| Example 17 | 50/10 | 1500/10 |
| Example 18 | 50/10 | 1500/10 |
| Example 19 | 50/10 | 1500/10 |

Drying: The wet pellets obtained from the spheronization step were then collected in a disposable weighing boat and dried overnight at 40° C. in a drying cabinet.

Dissolution of Adalimumab from Dried Pellets
  A quantity of adalimumab loaded pellets was placed in a 5 ml cryo tube and 4.0 ml of buffer was added to yield a theoretical 1 mg/ml adalimumab concentration, based on the theoretical calculated adalimumab loading. Citrate-TRIS buffer pH 7 was used unless stated otherwise. Samples are agitated during the entire duration of the experiment. Supernatant samples (200 µl) were taken at predetermined time points, centrifuged and the supernatant was analyzed in terms of total protein content, presence of aggregates (SEC) and fragmentation (electrophoresis) whenever specified.
  Total protein content quantification (Bradford): Total protein quantification was done by colorimetry following the Bradford method with a Coomassie Plus assay (Thermo Fisher Scientific). Briefly, 6.6 µl of sample were pipetted into to bottom of a 96-well plate and 200 µl of Coomassie Plus reagent were added and mixed by agitation for 30 s at 500 rpm. The samples were then incubated at room temperature for 10 min after which the absorbance at 595 nm was recorded (Tecan plate reader) and the blank subtracted. Quantification was done using a freshly prepared standard curve.

Microchip Electrophoresis analysis (fragments): The supernatant (2 μl) of samples containing adalimumab were tested for the presence of fragments by microchip gel electrophoresis under non-reducing conditions. In all experiments a positive control of adalimumab 1 mg/ml in citrate-TRIS buffer pH 7 was used.

Size exclusion chromatography (aggregation): The supernatant of samples containing adalimumab was tested for the presence of aggregates (dimers, oligomers) by size exclusion chromatography (SEC). In all experiments a positive control of adalimumab 1 mg/ml in citrate-TRIS buffer pH 7 was used.

Results

Comparative Experiment 1

Different test combinations of excipients together with adalimumab were processed into pellets, and adalimumab recovery as well as aggregation and fragmentation profiles were determined after individual processing steps. For one of the test compositions (Comparative Example 1:25% microcrystalline cellulose, 25% porous calcium carbonate/phosphate, 40% sorbitol, 10% sodium starch glycolate in the powder blend and 10 ml binding liquid containing 14.2 mg/ml adalimumab) the adalimumab recovery in citrate-TRIS buffer pH 7 is assessed after each process step and in the final pellets formulation (FIG. 1a), as well as the aggregation and fragmentation profile of samples collected at different time points is shown in FIG. 1b-c. As seen in FIG. 1b-c, no significant increase is observed in adalimumab aggregates or fragments after each process step when compared to an adalimumab standard.

Experiment 2

Figure 2:
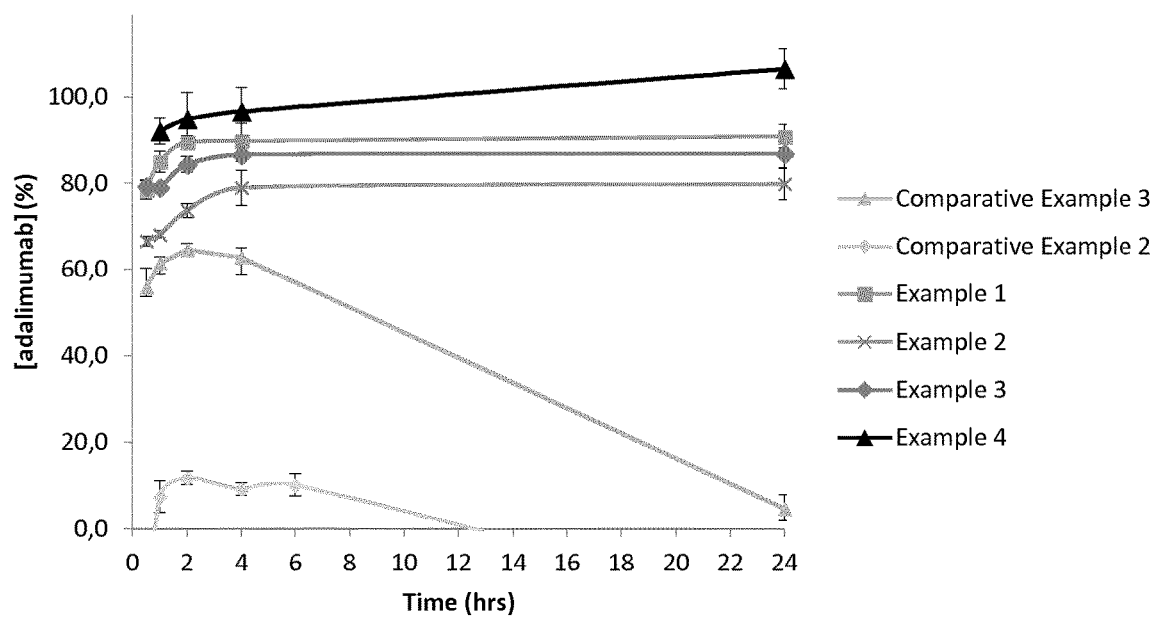
FIG. 2: Adalimumab release from pellets prepared with different concentrations of Tween® 20 or Kolliphor® 188 in the adalimumab containing binding liquid used for granulation. The excipients were the same as used in Comparative Example 2 pellets, except Example 1 and Comparative Example 3, which contained mannitol instead of sorbitol. Pellets dissolved in citrate-TRIS buffer pH 7. Total protein content on dissolution samples was determined colorimetrically using Bradford reagent. Results are expressed as mean of 3 replicates with corresponding standard deviations.

Adalimumab release from pellets containing the same excipient composition in the powder blending stage but granulated with different binding liquid compositions was assessed in citrate-TRIS buffer pH 7. Pellet compositions as listed in Table 1 were prepared as described above and tested. Using 0.01% Tween 20 as surfactant in the binding liquid during wet mixing/granulation significantly improved adalimumab recovery (Comparative Example 3) in comparison to the control formulation containing no surfactant (Comparative Example 2), however, it was not enough to prevent adsorption over time during dissolution. Using 0.05% (Example 1) or 0.1% Tween® 20 (Example 4) further increased recovery adalimumab, allowing a complete recovery when 0.1% Tween® 20 was used in the binding liquid containing adalimumab during the wet mixing (FIG. 2).

Figure 3:
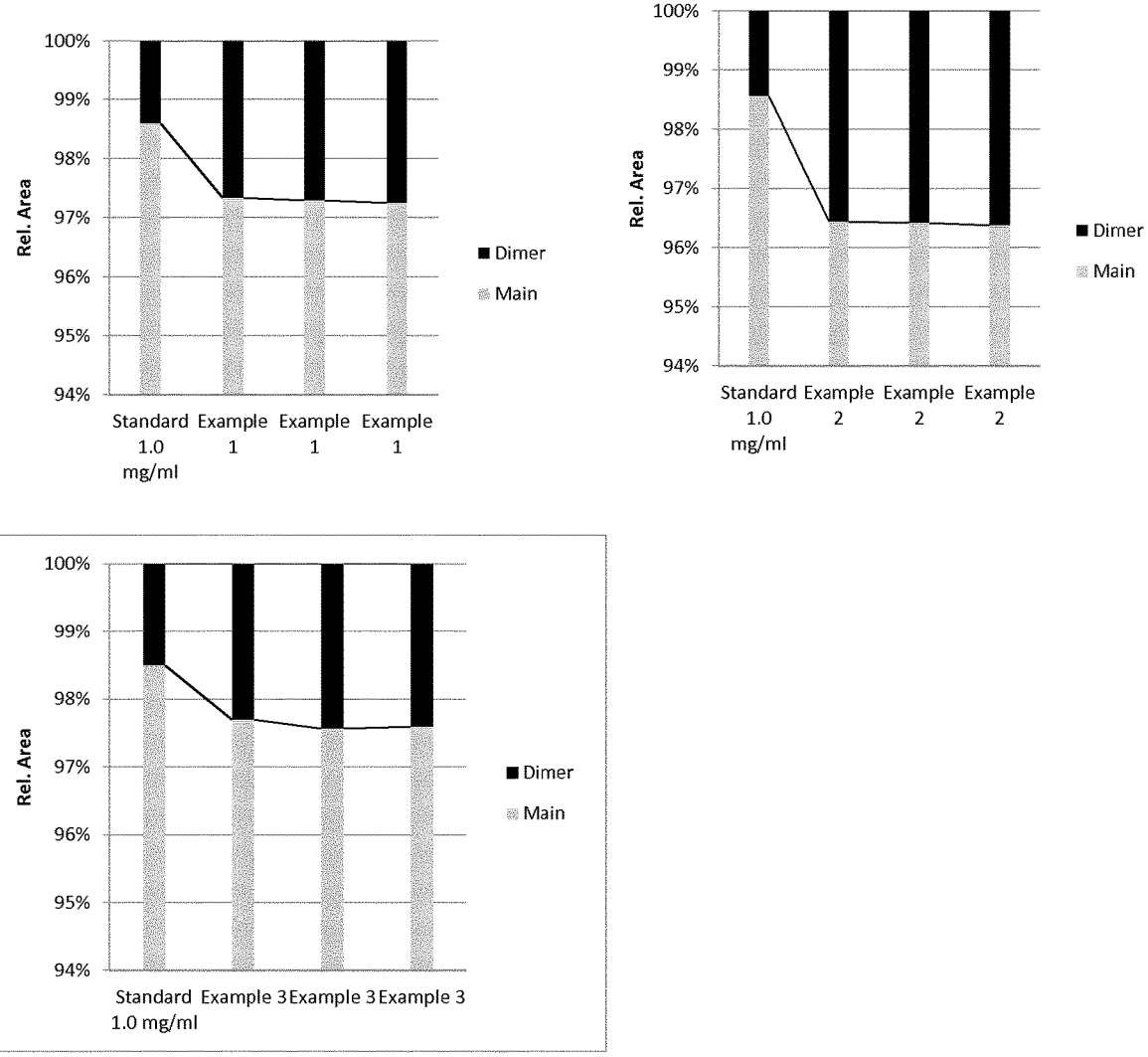
FIG. 3: Size exclusion chromatography (aggregates) data from adalimumab recovered after 24 h from Example 1, Example 2 and Example 3 pellets (immediate release) in citrate-TRIS buffer pH 7. Samples were prepared in triplicates and compared to a positive control of 1.0 mg/ml adalimumab in the same buffer.
Figure 4:
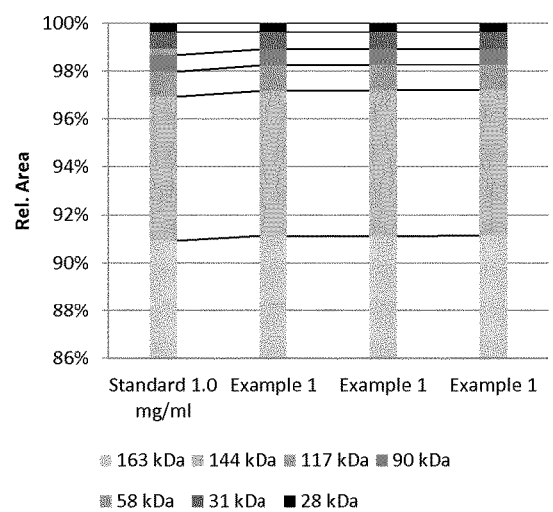
FIG. 4: Microchip electrophoresis (fragments) data from adalimumab recovered after 24 h from Example 1, Example 2 and Example 3 pellets in citrate-TRIS buffer pH 7. Samples were prepared in triplicates and compared to a positive control of 1.0 mg/ml adalimumab in the same buffer.
Figure 4:
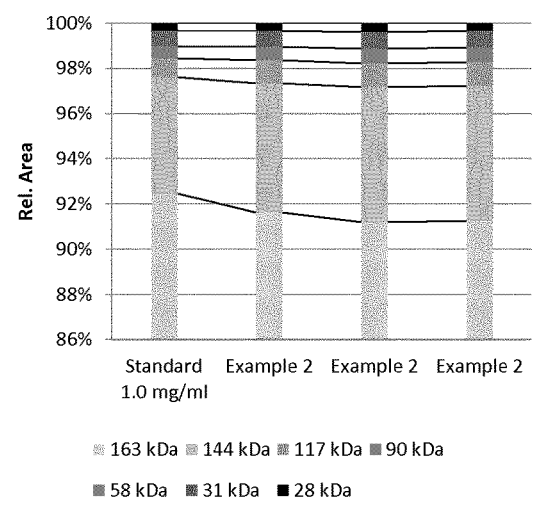
Figure 4:
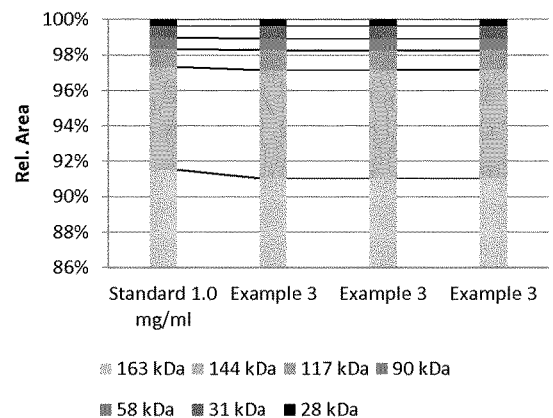

At 0.05%, Kolliphor® (Example 3) and Tween® 20 (Example 1) were equivalent in terms of adalimumab recovery an increase in concentration of Kolliphor® to 0.2% (Example 2) did not have an added benefit. Besides the improved adalimumab recovery when a surfactant was added to the binding liquid during in the granulation step as in Examples 1-4, no significant effects were seen in terms of aggregation (FIG. 3) and fragmentation (FIG. 4) in comparison to the adalimumab standard, indicating the sustainability of the formulation composition and the process to manufacture antibody solid dosage forms using an extrusion-spheronization process. The release from pellets comprising 50% Avicel, 30% Explotab® and 20% sorbitol (Example 4) led to a fast adalimumab release with more than 80% recovered within 2 h (FIG. 2 and FIG. 5 (B)).

The release from pellets comprising 70% Avicel® and as the sustained release polymer 5% Polyox® N-10 NF or Methocel K4M (Example 5 and Example 6) slowed down the initial burst release considerably and resulted in prolonged release of adalimumab. An increase in the content of Avicel® from 70% (Example 5) to 80% (Example 7) in formulations containing the sustained release polymer 5% Polyox® N-10 NF resulted in a significant slower release due to slower pellet disintegration.

TABLE 1

Immediate release solid dosage form formulation tested

| Batch | Conc. Tween® 20/Kolliphor® 188[1] (w/v) | Avicel® PH101 (%) | Explotab® (%) | Sorbitol (%) | Volume binding liquid (ml) |
| --- | --- | --- | --- | --- | --- |
| Comparative Example 2 | 0 | 50 | 30 | 20 | 17 |
| Example 1 | 0.05 | | | 23 | |
| Comparative Example 3 | 0.01 | | | | 20 |
| Example 2 | 0.2[1] | | | | 20 |
| Example 3 | 0.05[1] | | | | 22 |
| Example 4 | 0.1 | | | | 25 |

TABLE 2

Figure 5:
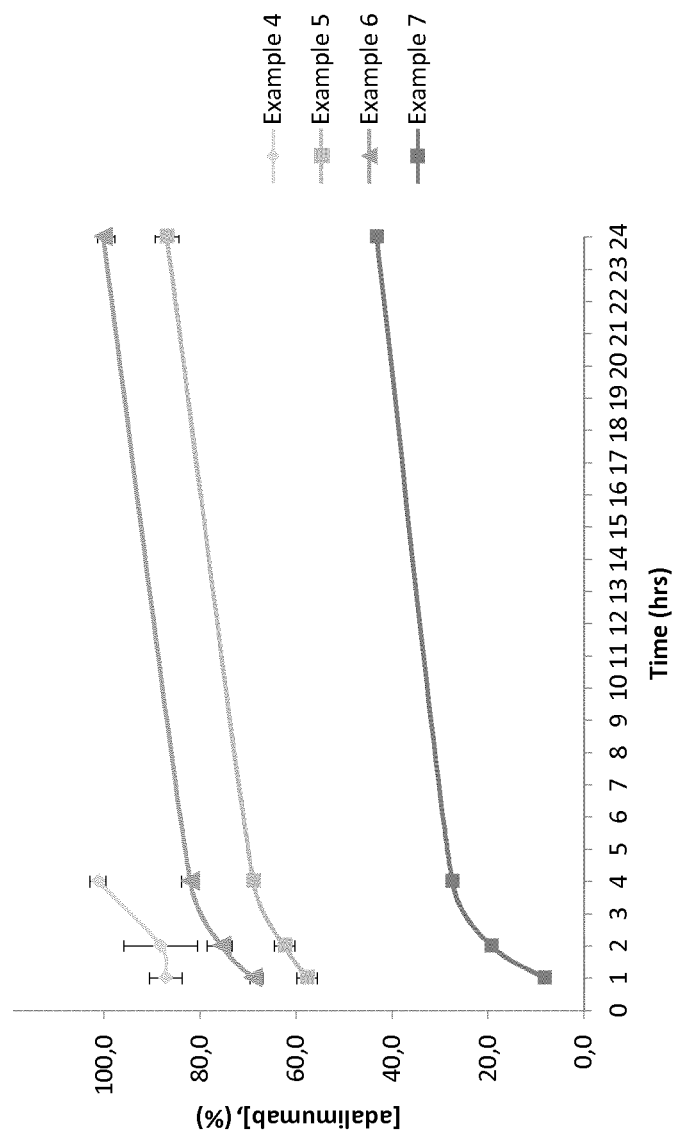
FIG. 5: Adalimumab release in citrate-TRIS buffer pH 7.0 from Example 4, Example 5, Example 6 and Example 7 pellets. Results are expressed as mean of 3 replicates with corresponding standard deviations.

Sustained release solid dosage form formulation tested (see FIG. 5)

| Composition ID | Conc. Tween 20 (w/v) | Avicel PH101 (%) | Explotab® (%) | Sorbitol (%) | Polyox® N-10 NF/Methocel K4M* (%) |
| --- | --- | --- | --- | --- | --- |
| Example 4 | 0.1 | 50 | 30 | 20 | — |
| Example 5 | 0.1 | 70 | 25 | — | 5 |
| Example 6 | 0.1 | 70 | 25 | — | 5* |
| Example 7 | 0.1 | 80 | 15 | — | 5 |

TABLE 3

Figure 6:
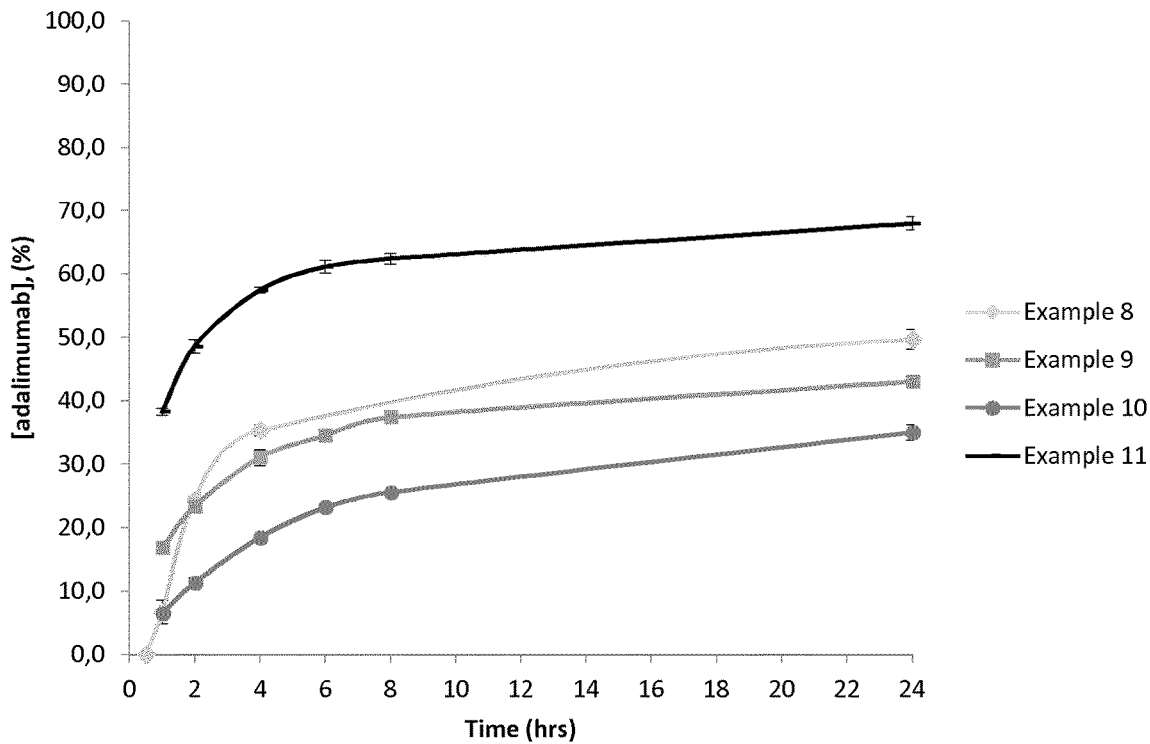
FIG. 6: (A) Adalimumab release in citrate-TRIS buffer pH 7.0 of different sustained release pellets. Results are expressed as mean of 3 replicates with correspondent standard deviation. (B) Dissolution in citrate TRIS buffer pH 7 of different sustained release pellets comprising Compritol® ATO 188 as sustained release polymer.
Figure 6:
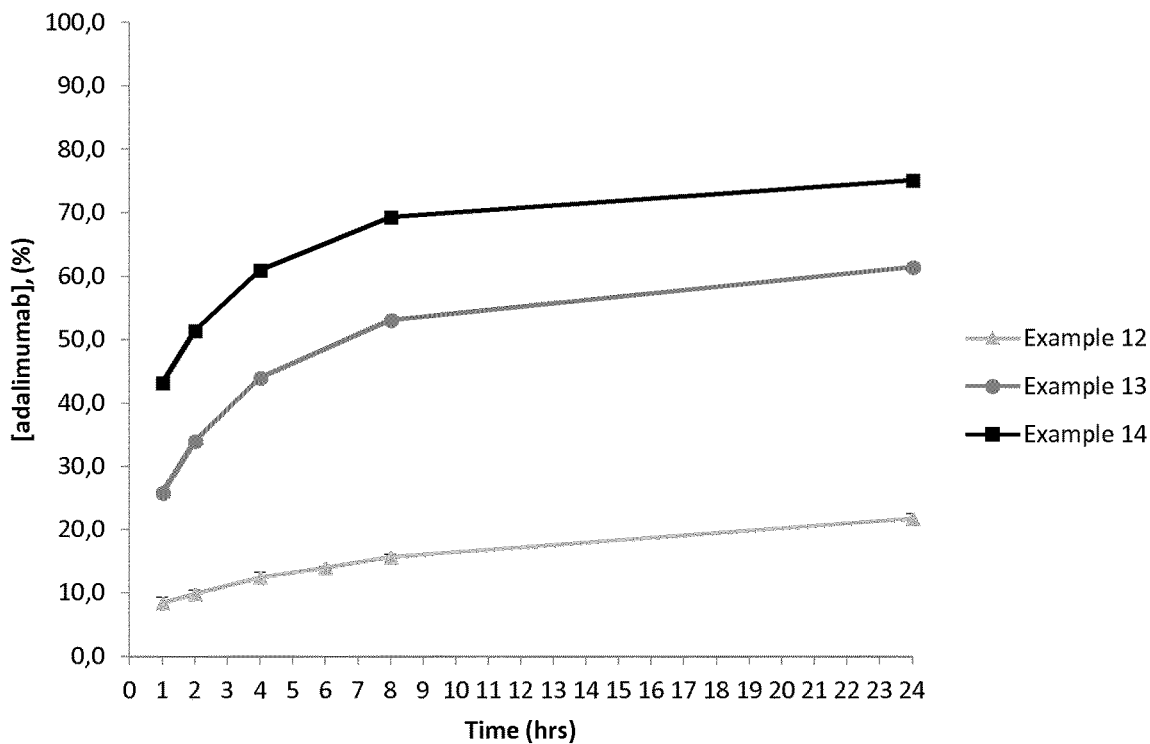

Sustained release solid dosage form formulation tested (see FIG. 6)

| Composition ID | Conc. Tween 20 (m/v) | Avicel PH101 (%) | Explotab ®/Starch 1500* (%) | Sorbitol (%) | Polyox ® N-10 NF (%) |
|---|---|---|---|---|---|
| Example 8 | 0.1 | 75 | 10 | 10 | 5 |
| Example 9 | 0.2 | 75 | 10 | 10 | 5 |
| Example 10 | 0.1 | 75 | 10* | 10 | 5 |
| Example 11 | 0.15 | 75 | 10 | 10 | 5 |

Experiment 3

Further pellet compositions for sustained release dosage forms were tested, where sorbitol was added at the cost of the disintegrant (Explotab®) and the volume of surfactant was further varied (FIG. 6). This revealed that the release of adalimumab in the first 4 h after immersion could be further slowed down. The adalimumab dissolution in buffer pH 7.0 from the pellets of batch Example 10, containing Starch 1500 instead of Explotab® (Example 8) on the other hand was very slow with less than 30% recovery within 24 h (FIG. 6). Increasing the Tween® 20 concentration from 0.1% (Example 10) to 0.2% (Example 9) resulted in a slightly faster drug release (FIG. 6).

Experiment 4

Compritol® 888 ATO was tested as a sustained release polymer, otherwise using the components and preparation as described above for the other sustained release dosage forms (0.1% Tween® 20). The following pellet compositions were prepared and tested.

TABLE 4

Sustained release solid dosage forms with Compritol ® ATO 188

| Composition ID | Conc. Tween 20 (w/v) | Avicel PH101 (%) | Compritol ATO 188 | Sorbitol |
|---|---|---|---|---|
| Example 12 | 0.1 | 75 | 25 | 0 |
| Example 13 | 0.1 | 75 | 10 | 15 |
| Example 14 | 0.1 | 75 | 5 | 20 |

Pellets containing 75% Avicel PH101 in combination with 25% Compritol ATO 188 led to a continuous but slow release over the course of 24h (Example 12). This was improved considerably by reducing the amount of Compritol ATO 188 to 10% or 5% (Example 13 and Example 14, respectively).

Experiment 5

TABLE 5 immediate release solid dosage forms prepared with spray-dried adalimumab added during dry mixing

| Composition ID | Avicel ® PH101 (%) | Explotab ® (%) | Sorbitol (%) | Spray-dried Adalimumab (%) | Concentration Tween ® 20 (% w/v) |
|---|---|---|---|---|---|
| Comparative example 4 | 45 | 10 | 36.6 | 8.4 | 0.1 |

TABLE 5-continued immediate release solid dosage forms prepared with spray-dried adalimumab added during dry mixing

| Composition ID | Avicel ® PH101 (%) | Explotab ® (%) | Sorbitol (%) | Spray-dried Adalimumab (%) | Concentration Tween ® 20 (% w/v) |
|---|---|---|---|---|---|
| Example 15 | 45 | 10 | 36.6 | 8.4 | 0.25 |
| Example 16 | 45 | 10 | 36.6 | 8.4 | 0.5 |

Figure 7:
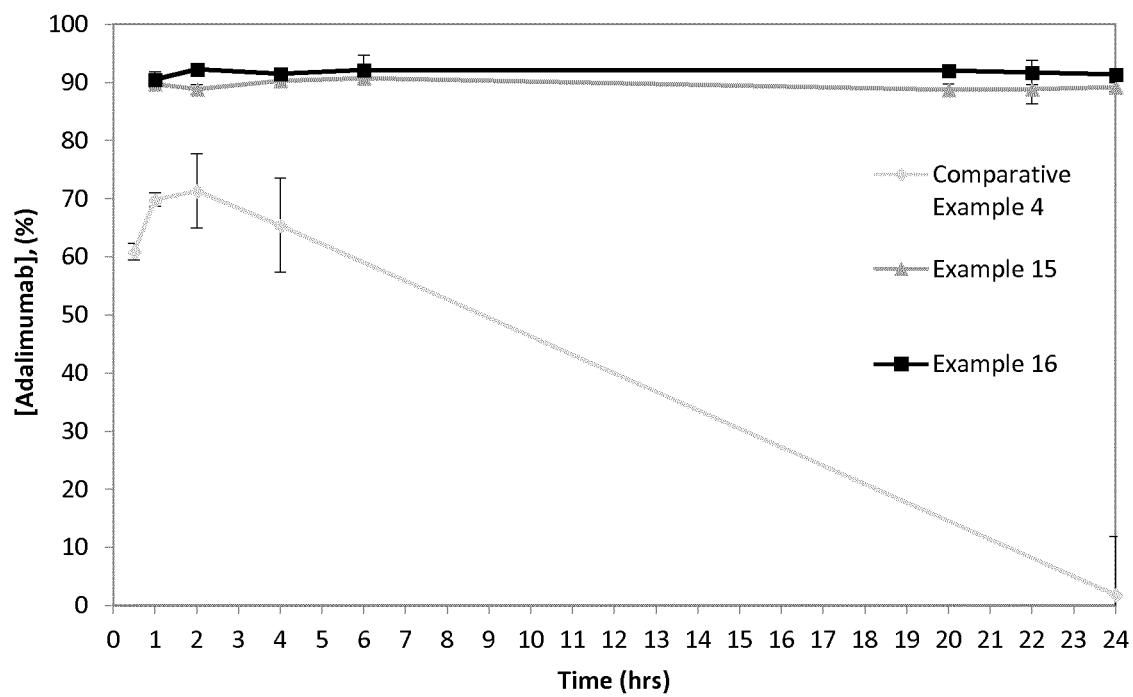
FIG. 7: Adalimumab release from immediate release pellets prepared by adding adalimumab directly into the powder blend and using different Tween® 20 concentrations (0.1% Tween® 20 (Comparative Example 4), 0.25% Tween® 20 (Example 15) and 0.5% Tween® 20 (Example 16) in the binding liquid.

Pellets were also prepared starting with spray-dried adalimumab in the dry blending stage. In this case the binding liquid is an aqueous solution of Tween® 20 at different concentrations, ranging from 0.1% to 0.5% w/v. Increasing Tween® 20 concentration in the binding liquid resulted in fast dissolution with about 90% adalimumab recovered from the pellets, in comparison to pellets manufactured with only 0.1% Tween® 20 (Comparative Example 4), where adalimumab could not be recovered even over a longer time period due to adsorption (FIG. 7).

Experiment 6

Figure 8:
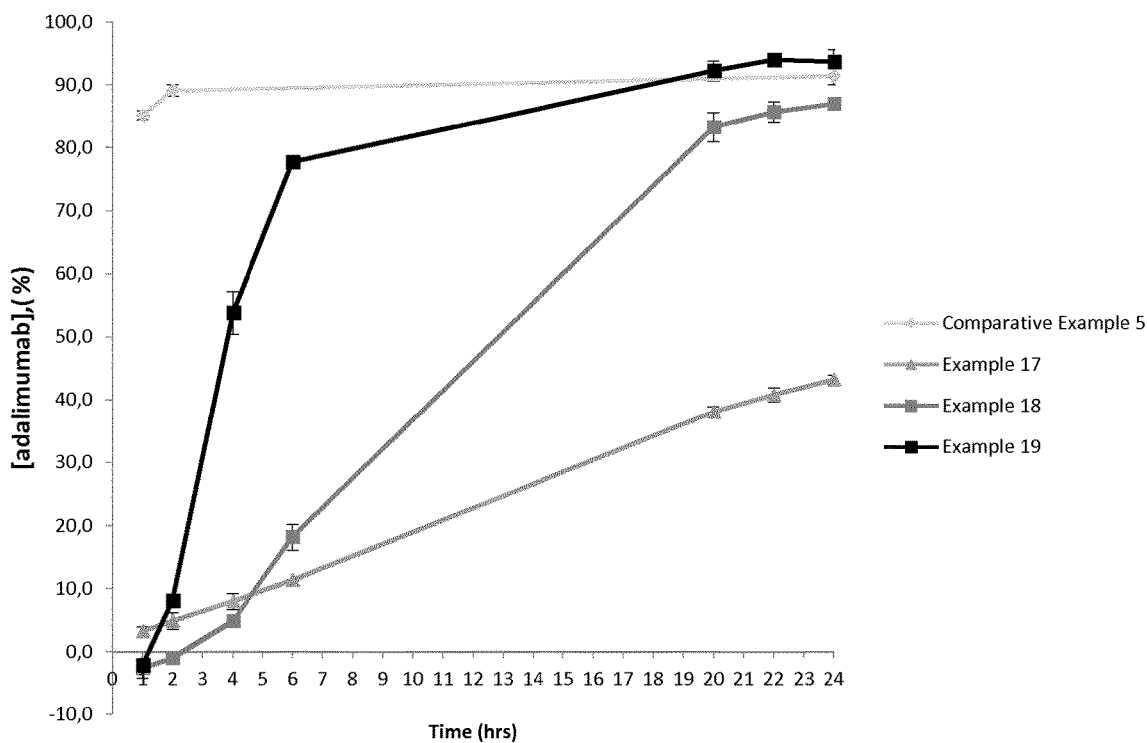
FIG. 8: Adalimumab release from Immediate release adalimumab loaded pellets (Comparative Example 5), prepared by extrusion-spheronization, were further coated in a fluid bed equipment with a sustained release coating comprising Eudragit® RS 30D, triethyl citrate as plasticizer and Syloid® 244FP as anti-tacking to a polymer weight gain of 28.5% (Example 17), 20.6% (Example 18) and 13.7% (Example 19). Additionally, no significant increase in adalimumab aggregates or fragments was observed in Example 19 pellet samples collected after 24 h in dissolution, as determined by size exclusion chromatography and microchip electrophoresis, respectively (FIG. 8B)
Figure 8:
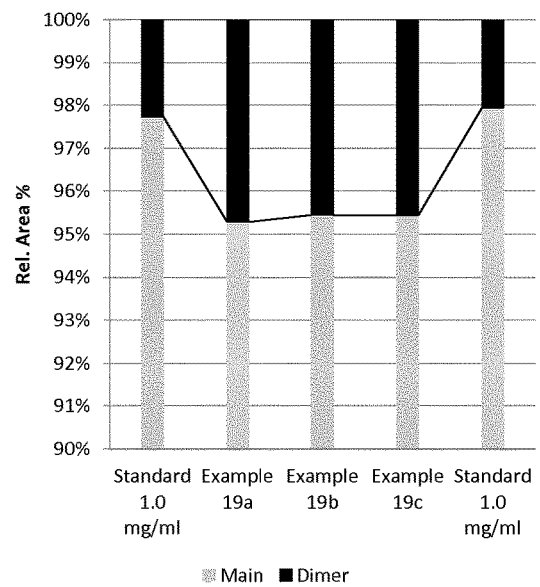
Figure 8:
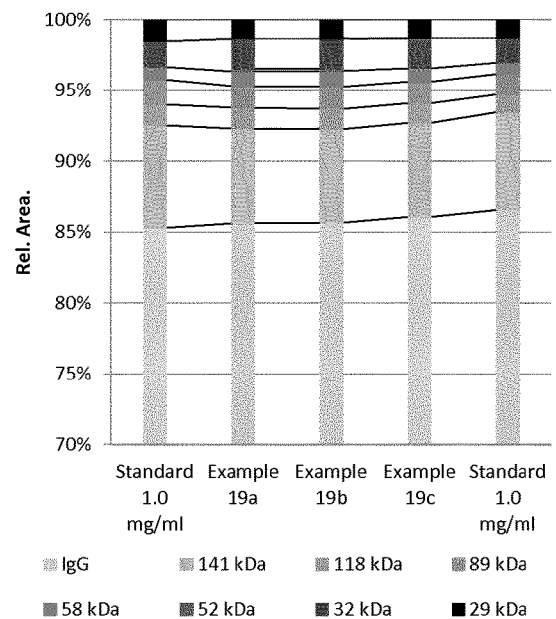

Immediate release adalimumab loaded pellets (Comparative Example 5), prepared by extrusion-spheronization, were further coated in a fluid bed equipment with a sustained release coating comprising Eudragit® RS 30D, triethyl citrate (20% based on polymer) as plasticizer and Syloid® 244FP (10% based on polymer) as anti-tacking to a polymer weight gain of 28.5% (Example 17), 20.6% (Example 18) and 13.7% (Example 19). Adalimumab release in citrate-TRIS buffer pH 7 from the matrix pellets could be effectively controlled by the Eudragit® RS 30D coating quantity applied on the adalimumab layered pellets (FIG. 8A). Additionally, no significant increase in adalimumab aggregates or fragments was observed in Example 19 pellet samples collected after 24 h in citrate-TRIS buffer pH 7, as determined by size exclusion chromatography and microchip electrophoresis, respectively (FIG. 8B), indicating that both the formulation and the manufacture steps, including the extrusion-spheronization process followed by a coating with sustained release polymer do not have a detrimental impact on the antibody.

The invention claimed is:

1. A method for preparing a solid dosage form selected from tablets, capsules, caplets, pills, pellets, sachets and granules comprising at least one antibody or functional fragment thereof, a surfactant, an extrusion-spheronization aid, a buffer, a disintegrant and at least one further excipient selected from the group consisting of fillers, sustained release agents and combinations thereof, said method comprising the steps of:

a) providing a powder blend comprising the extrusion-spheronization aid, the disintegrant, and the at least one further excipient;
b) adding a binding liquid to the powder blend of step a) and granulating to obtain a wet mass;
c) extruding the wet mass of step b) and collecting an extrudate;
d) spheronizing the extrudate of step c) to obtain wet spheroids; and
e) drying the wet spheroids to obtain the solid dosage form;

wherein:
  (i) the at least one antibody or functional fragment thereof, the buffer, and the surfactant are contained within the powder blend and/or the binding liquid,
  (ii) the amount of surfactant relative to the total volume of the binding liquid (w/v) is from 0.05 to 0.2%, further wherein the surfactant is selected from the group consisting of polysorbate 20, polysorbate 28, polysorbate 40, polysorbate 60, polysorbate 65, polysorbate 80, polysorbate 81, polysorbate 85, poloxamer 124, poloxamer 181, poloxamer 188, poloxamer 237, poloxamer 331, poloxamer 338 and poloxamer 407, glyceryl monostearate, polyethoxylated castor oil, PEG-40 hydrogenated castor oil, macrogol 15 hydroxystearate, polyoxyl 15 Hydroxystearate, caprylocaproyl macrogol-8 glyceride, D-α-tocopherol polyethylene glycol 1000 succinate, glycerol monostearate, lecithin, sorbitan monopalmitate, cetyl alcohol oleyl alcohol sodium glycolate, sodium de(s)oxycholate, alkyl glycoside, polyethylene glycol, polpropylene glycol, alkyl poly (ethylene oxide), alkyl polyglucoside, octyl glucoside, decyl maltoside, and combinations thereof,
  (iii) the extrusion-spheronization aid is selected from the group consisting of microcrystalline cellulose, hydroxypropylmethylcellulose (HPMC), hydroxyethylcellulose, cyclodextrin, pectin, pectinic acid, starch, dextrins, carrageenan, glycerol monostearate and colloidal silica dioxide;
  (iv) the disintegrant is selected from the group consisting of sodium starch glycolate, croscarmellose sodium, cross-linked polyvinylpyrrolidone, soy polysaccharide, cross-linked alginic acid and combinations thereof, and
  (v) the at least further excipient comprises (a) a filler selected from the group consisting of dextrose, lactose, lactose monohydrate, lactose anhydrous, xylitol, mannitol, sucrose, glucose, raffinose, sorbitol, trehalose, dicalcium phosphate, propyleneglycol, polyethylene glycol, and amino acids selected from among arginine, histidine, glycine, alanine, lysine, proline, leucine, glutamic acid, serine, aspartic acid, and asparagine, and respective salts thereof, and/or (b sustained release agents selected from the group consisting of nonionic poly(ethylene oxide) polymers with a molecular weight between 100,000 and 7,000,000, HPMC 2208 type with a viscosity at 2 wt.-% in water at 20° C. between 3 and 100,000 mPa·s, xanthan gum, guar gum, tragacanth gum, locust bean gum, acacia gum, chitosan, carbomers, glycerol (di)behenate, glyceryl palmitostearate, ethylcellulose, Polyvinyl acetate and polymethacrylates selected from among poly(ethyl acrylate, methyl methacrylate, trimethylammonioethyl methacrylate chloride) 1:2:0.1, poly(ethyl acrylate, methyl methacrylate, trimethylammonioethyl methacrylate chloride) 1:2:0.2, or poly(ethylacrylate, methylmethacrylate) 2:1.

2. The method according to claim 1, wherein the powder blend of step a) or the binding liquid of step b) further comprises a binder.

3. The method according to claim 1, wherein the at least one further excipient is a filler selected from the group consisting of dextrose, mannitol, sorbitol, xylitol, trehalose, sucrose, amino acids such as arginine, histidine, glycine, alanine, lysine, proline, leucine, glutamic acid, serine, aspartic acid and asparagine, and respective salts thereof, dicalcium phosphate, and combinations thereof.

4. The method according to claim 3, further comprising, after step e), the step of:
f) applying at least one additional coating in the form of a sustained release coating.

5. The method according to claim 4, wherein the sustained release coating comprises at least one sustained release polymer selected from the group consisting of polymethacrylates such as poly (ethyl acrylate, methyl methacrylate, trimethylammonioethyl methacrylate chloride) 1:2:0.1, poly (ethyl acrylate, methyl methacrylate, trimethylammonioethyl methacrylate chloride) 1:2:0.2, or poly (ethylacrylate, methylmethacrylate) 2:1, ethylcellulose, polyvinyl acetate, and combinations thereof.

6. The method according to claim 1, wherein the solid dosage form is a sustained release solid dosage form, and wherein the at least one further excipient comprises at least one sustained release agent, selected from the group consisting of nonionic poly (ethylene oxide) polymers with a molecular weight between 100,000 and 7,000,000, HPMC 2208 type with a viscosity at 2 wt.-% in water at 20° C. between 3 and 100,000 mPa·s, xanthan gum, guar gum, tragacanth gum, locust bean gum, acacia gum, chitosan, carbomers, ethylcellulose, polyvinyl acetate, glyceryl (di) behenate, glyceryl palmitostearate, polymethacrylates selected from among poly (ethyl acrylate, methyl methacrylate, trimethylammonioethyl methacrylate chloride) 1:2:0.1, poly (ethyl acrylate, methyl methacrylate, trimethylammonioethyl methacrylate chloride) 1:2:0.2, or poly (ethylacrylate, methylmethacrylate) 2:1, and combinations thereof.

7. The method according to claim 1, wherein said solid dosage further comprises at least two further excipients in addition to the disintegrant, wherein a first further excipient is a sustained release agent and a second further excipient is a filler.

8. The method according to claim 1, wherein the solid dosage form comprises from 0.05 to 60% of the at least one antibody or functional fragment thereof relative to the total weight of the solid dosage form after step e).

9. The method according to claim 1, wherein the at least one antibody or functional fragment thereof is selected from among (a) antibodies specific to tumor necrosis factor alpha (TNFα) and functional fragments thereof, (b) antibodies specific to α4β7 integrin and functional fragments thereof, (c) antibodies specific to CD3, CD4 or CD20 and functional fragments thereof, (d) antibodies specific to interleukin 6 (IL-6), interleukin 12 (IL-12), interleukin 13 (IL-13), interleukin 23 (IL-23) or to their receptors and functional fragments thereof, (e) antibodies specific to CXCL10/IP-10 and functional fragments thereof, and (f) antibodies specific to p40 protein subunit and functional fragments thereof.

10. The method according to claim 9, wherein the antibody or functional fragment thereof is selected from the group consisting of: infliximab, adalimumab, etanercept, certolizumab pegol and golimumab and functional fragments thereof.

11. The method according to claim 1, wherein at any time during steps a) to d), the temperature of the at least one antibody or functional fragment thereof is lower than 50° C., and wherein during step e) the drying of the wet spheroids is carried out at a temperature lower than 50° C.

12. The method according to claim 1, further comprising, after step e), or after step f) if at least one additional coating in the form of a sustained release coating is applied as step f), the step of applying at least one additional coating in the form of a delayed release coating, further wherein the solid dosage form is formulated oral administration.

13. The method according to claim 12, wherein the delayed release coating comprises at least one component selected from the group consisting of poly vinyl acetate phthalate, cellulose acetate trimellitate, hydroxypropyl methylcellulose phthalate HP-50, HP-55 or HP-55S, cellulose acetate phthalate, hydroxypropyl methylcellulose acetate succinate (HPMCAS), poly (methacrylic acid, ethyl acrylate) 1:1, poly (methacrylic acid, methyl methacrylate) 1:1, poly (methacrylic acid, methyl methacrylate) 1:2, chondroitin sulfate, pectin, guar gum, chitosan, Inulin, lactulose, raffinose, stachyose, alginate, dextran, xanthan gum, locust bean gum, arabinogalactan, amylose, amylopectin, pullulan, carrageenan, cyclodextrin, scleroglucan, chitin, curdulan, levan, starch, resistant starch, azo compounds being degraded by azo bonds splitting bacteria, and combinations thereof.

14. The method according to claim 12, wherein, upon oral administration of the solid dosage form, the release of the antibody or functional fragment starts in the terminal ileum, the ileocolonic region, the ascending colon, transverse colon or the descending colon.

15. The method of claim 6, wherein said sustained release agent is a nonionic poly (ethylene oxide) polymer with a molecular weight between 100,000 and 7,000,000, HPMC 2208 type with a viscosity at 2 wt.-% in water at 20° C. between 2,663 and 4,970 mPa·s.

16. The method of claim 1, wherein the solid dosage form comprises from 1 to 20% of the at least one antibody or functional fragment thereof relative to the total weight of the solid dosage form after step e).

* * * * *